United States Patent
Iosifidis et al.

(10) Patent No.: US 11,559,517 B2
(45) Date of Patent: Jan. 24, 2023

(54) PROMOTION OF EPITHELIAL REPAIR

(71) Applicants: Telethon Kids Institute, Nedlands (AU); The University of Newcastle, Callaghan (AU)

(72) Inventors: Thomas Iosifidis, Nedlands (AU); Anthony Kicic, Nedlands (AU); Darryl Knight, Callaghan (AU); Stephen Stick, Nedlands (AU)

(73) Assignee: Telethon Kids Institute, Nedlands (AU)

( * ) Notice: Subject to any disclaimer, the term of this patent is extended or adjusted under 35 U.S.C. 154(b) by 19 days.

(21) Appl. No.: 17/057,156

(22) PCT Filed: May 21, 2019

(86) PCT No.: PCT/AU2019/050493
§ 371 (c)(1),
(2) Date: Nov. 20, 2020

(87) PCT Pub. No.: WO2019/222801
PCT Pub. Date: Nov. 28, 2019

(65) Prior Publication Data
US 2021/0196687 A1    Jul. 1, 2021

(30) Foreign Application Priority Data
May 21, 2018   (AU) ................................ 2018901783

(51) Int. Cl.
*A61K 31/42* (2006.01)
*A61P 11/06* (2006.01)
*A61P 11/16* (2006.01)
*A61K 31/18* (2006.01)
*A61K 31/415* (2006.01)

(52) U.S. Cl.
CPC .............. *A61K 31/42* (2013.01); *A61K 31/18* (2013.01); *A61K 31/415* (2013.01); *A61P 11/06* (2018.01); *A61P 11/16* (2018.01)

(58) Field of Classification Search
CPC ...... A61K 31/18; A61K 31/415; A61K 31/42; A61K 31/635; A61P 11/06; A61P 11/16; A61P 17/02; A61P 37/00; A61P 3/10
See application file for complete search history.

(56) References Cited

FOREIGN PATENT DOCUMENTS

WO    2017/075715 A1    5/2017

OTHER PUBLICATIONS

Hamdulay et al., "Celecoxib activates PI-3K/Akt and mitochondrial redox signaling to enhance heme oxygenase-1-mediated anti-inflammatory activity in vascular endothelium," Free Radical Biology & Medicine, 48: 1013-1023 (2010).
Lai et al., "Phosphatase and tensin homologue deleted on chromosome ten (PTEN) as a molecular target in lung epithelial wound repair," British Journal of Pharmacology, 152: 1172-1184 (2007).

(Continued)

*Primary Examiner* — Savitha M Rao
(74) *Attorney, Agent, or Firm* — Morgan, Lewis & Bockius, LLP

(57) ABSTRACT

There is provided a method for promoting epithelium repair in a subject, the method comprising administering to the subject a therapeutically effective amount of an activator of PI3K/Akt signalling.

8 Claims, 14 Drawing Sheets

(56) References Cited

OTHER PUBLICATIONS

Bao et al., "Keratinocyte growth factor induces Akt kinase activity and inhibits Fas-mediated apoptosis in A549 lung epithelial cells," American Journal of Physiology-Lung Cellular and Molecular Physiology, 288: L36-L42 (2005).
International Search Report issued in corresponding International Patent Application No. PCT/AU2019/050493 dated Nov. 18, 2019.
Written Opinion issued in corresponding International Patent Application No. PCT/AU2019/050493 dated Jun. 21, 2019.
Extended European Search Report issued in corresponding European Patent Application No. 19807850.3 dated Feb. 2, 2022.
Iosifidis et al., "Aberrant cell migration contributes to defective airway epithelial repair in childhood wheeze," JCI Insight, 5 (7): e133125 (2020).

A

B

PROMOTION OF EPITHELIAL REPAIR

TECHNICAL FIELD

The technology relates to the use of activators of PI3K/Akt signalling for promoting repair of epithelium, particularly in the airways of asthmatic subjects.

RELATED APPLICATION

This application claims priority to Australian provisional patent application No 2018901783 filed 21 May 2018 which is herein incorporated by reference in its entirety.

BACKGROUND

Asthma is a substantial global health care burden with around 300 million individual sufferers, despite substantial progress in our understanding of its pathophysiology. Asthma is the most common chronic respiratory disorder in children. Although the symptoms of asthma are potentially manageable in most asthma sufferers using conventional therapeutic regimens such as topical bronchodilators and corticosteroids, these regimens fail to alter the underlying pathogenesis and present unwanted side effects. As such, there is a pressing need for identification of novel therapeutic strategies that target the principal cause of asthma and not just its clinical sequelae.

Airway remodeling in asthma, characterized as thickening of the airway mucosa, has been associated with dysregulated responses of tissue repair and regeneration to injury. These impairments have been shown to be present from early childhood, not necessarily subsequent to but rather in parallel with airway inflammation. Importantly, the airway epithelium constitutes the first barrier of defense that protects the internal milieu of the lung against foreign factors. Therefore, it is likely that underlying defective cellular mechanisms in children with asthma predispose the airways to damage, unresolved inflammation, and subsequent airway remodeling and persistent asthma symptoms.

Following injury, a rapid and coordinated reparative response is elicited to maintain epithelial barrier integrity and prevent secondary damage to the host. Physiological airway wound repair is characterized by initial cell spreading and migration into the wound site, specifically of a finite number of rows of epithelial cells surrounding the wound, termed 'leading edge cells'. This is followed by basal cell proliferation and differentiation into various epithelial cell subtypes. Similar to other epithelial linings, migration of epithelial cells after airway damage has been shown to close small wounds without the need for cell proliferation, whereas repair of large wounded areas requires both proliferation and migration. Airway epithelium from children with asthma is hyperproliferative compared to that from non-asthmatic controls.

Repair of airway epithelium from children with asthma is impaired by, and associated with, deficient production of the extracellular matrix (ECM) protein, fibronectin (FN) and is partially restored by application of exogenous FN. Epithelial cells at the leading edge of the wound adhere to ECM proteins and mediate forward and directional movement of the epithelial cell sheet via binding of integrins. Airway epithelial cells express FN-binding integrins, which are essential for efficient migration and re-epithelisation of wounds and airway epithelia of adults diagnosed with asthma display reduced expression of integrin β4. However, whether dysregulation of integrin related pathways plays an important role in the pathobiology of asthma is uncertain.

Regardless of anatomical location or function, all breaches of the epithelia must be repaired quickly, not only to prevent ingress of pathogens or harmful materials to the body but also to prevent fluid loss.

It is widely accepted that the airway epithelium plays a central role in the pathogenesis of asthma and treatments improving airway epithelial barrier integrity and regeneration post wounding could lead to significant improvements in the quality of life of asthmatic patients, as well as prevent future lung damage and irreversible airway remodeling.

The present inventors have identified that defective cell migration and repair of the airway epithelium of children with asthma can be rescued via stimulation of the PI3K-Akt-integrin α5β1 axis. This can be targeted with therapeutics that activate PI3K-Akt signaling.

DISCLOSURE OF INVENTION

In a first aspect there is provided a method for promoting epithelium repair in a subject, the method comprising administering to the subject a therapeutically effective amount of an activator of PI3K/Akt signalling.

In a second aspect there is provided use of an activator of PI3K/Akt signalling for the manufacture of a medicament for promoting epithelium repair in a subject.

In one embodiment the epithelium is selected from airway epithelium, mesothelium, endothelium, stratified epithelium, stratified ciliated and columnar epithelia. For example the epithelium is stratified epithelium of the skin or airway epithelium.

In some embodiments the activator enhances expression of α5β1 integrin in an epithelial cell of the subject.

The activator may be selected from the group consisting of celecoxib, dimethyl-celecoxib, SC-58125 (5-(4-fluorophenyl)-1-[4-(methylsulfonyl)phenyl]-3-(trifluoromethyl)-1H-pyrazole), valdecoxib, rofecoxib, 3-trifluoromethyl-5-(p-tolyl)-1H-pyrazole, SC-58236 (4-[5-(4-chlorophenyl)-3-(trifluoromethyl)-1H-pyrazol-1-yl] benzenesulfonamide), sulfanilamide, OSU-03012 (AR-12,2-Amino-N-[4-[5-(2-phenanthrenyl)-3-(trifluoromethyl)-1H-pyrazol-1-yl]phenyl]acetamide), sulfasalazine, parecoxib sodium, piroxicam, NS-398 (N-[2-(Cyclohexyloxy)-4-nitrophenyl]methanesulfonamide), 4-[2-[1-(4-methylphenyl)ethylidene]hydrazinyl] benzenesulfonamide, hydroxy celecoxib, deracoxib, 4-desmethyl-3-methyl celecoxib, N-de(4-sulfonamidophenyl)-N'-(4-sulfonamidophenyl) celecoxib, 2,5-dimethyl-celecoxib, desmethyl celecoxib, celecoxib carboxylic acid, benzenesulfonamide, and SC-560 (5-(4-Chlorophenyl)-1-(4-methoxyphenyl)-3-trifluoromethyl pyrazole).

In an embodiment the activator is selected from celecoxib, dimethyl-celecoxib, parecoxib sodium, hydroxy celecoxib and NS-398.

In one embodiment the subject is a smoker.

In another embodiment the promotion of epithelial repair in the subject slows or reduces the progression of a disease or condition in the subject. The disease or condition may be one or more of asthma, diabetes, peripheral vascular disease, an autoimmune disorder, chronic inflammation, acute inflammation, a wound, or stress.

The wound may be a pressure ulcer, a decubitus ulcer, a venous ulcer, a burn, or a surgical wound.

In some embodiments the disease is asthma and the epithelium is airway epithelium. The subject may be an infant or child.

In one embodiment the subject may be an asthmatic child

In another embodiment the activator enhances expression of α5β1 integrin in an epithelial cell of the subject.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

Definitions

The following are some definitions of terms used in the art that may be helpful in understanding the description of the present invention. These are intended as general definitions and should in no way limit the scope of the present invention to those terms alone, but are put forth for a better understanding of the following description.

[Unless the context requires otherwise or specifically stated to the contrary, integers, steps, or elements of the invention recited herein as singular integers, steps or elements clearly encompass both singular and plural forms of the recited integers, steps or elements.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps, features, compositions and compounds.

The terms "treating", "treatment" and "therapy" are used herein to refer to curative therapy, prophylactic therapy, palliative therapy and preventative therapy. Thus, in the context of the present disclosure the term "treating" encompasses curing, ameliorating or tempering the severity of a medical condition or one or more of its associated symptoms.

The terms "therapeutically effective amount" or "pharmacologically effective amount" or "effective amount" refer to an amount of an agent sufficient to produce a desired therapeutic or pharmacological effect in the subject being treated. The terms are synonymous and are intended to qualify the amount of each agent that will achieve the goal of improvement in disease severity and/or the frequency of incidence over treatment of each agent by itself while preferably avoiding or minimising adverse side effects, including side effects typically associated with other therapies. Those skilled in the art can determine an effective dose using information and routine methods known in the art.

A "pharmaceutical carrier, diluent or excipient" includes, but is not limited to, any physiological buffered (i.e., about pH 7.0 to 7.4) medium comprising a suitable water soluble organic carrier, conventional solvents, dispersion media, fillers, solid carriers, coatings, antibacterial and antifungal agents, isotonic and absorption delaying agents. Suitable water soluble organic carriers include, but are not limited to, saline, dextrose, corn oil, dimethylsulfoxide, and gelatin capsules. Other conventional additives include lactose, mannitol, corn starch, potato starch, binders such as microcrystalline cellulose, cellulose derivatives such as hydroxypropylmethylcellulose, acacia, gelatins, disintegrators such as sodium carboxymethylcellulose, and lubricants such as talc or magnesium stearate.

"Subject" includes any human or non-human mammal. Thus, in addition to being useful for human treatment, the compounds of the present invention may also be useful for veterinary treatment of mammals, including companion animals and farm animals, such as, but not limited to dogs, cats, horses, cows, sheep, and pigs. In an embodiment the subject is a human. In various embodiments the subject is a human child or infant. In some embodiments the subject may be asthmatic.

In the context of this specification the term "administering" and variations of that term including "administer" and "administration", includes contacting, applying, delivering or providing a compound or composition of the invention to a subject by any appropriate means.

In order that the present invention may be more clearly understood, embodiments will be described with reference to the following drawings and examples.

DESCRIPTION OF EMBODIMENTS

Figure 1:
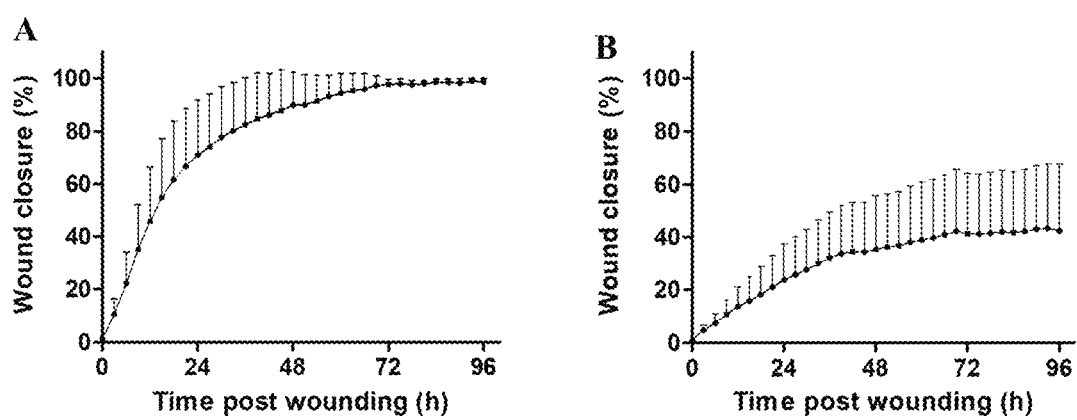
FIG. 1. Dysregulated wound closure in pAEC from children with asthma. (A) Monolayer pAEC cultures from non-asthmatic children were scratch wounded and wound closure rates were determined. pAEC cultures reached wound closure rates of 89.92±3.29% within 48 h post wounding where complete wound closure (100.00±1.89%) was achieved by 72 h post wounding. (B) pAEC cultures reached wound closure rates of 35.28±7.21% within 48 h post wounding where cells failed to close the wound by 96 h post wounding. Samples were collected from 14 non-asthmatic and 9 asthmatic children and the experiments were completed in two technical replicates; mean±SD.

The technology is based on the discovery that celecoxib and dimethyl-celecoxib activate PI3K/Akt signaling which increases α5β1 integrin expression in epithelial cells which in turn increases the rate of migration of those cells and promotes epithelial repair. Accordingly activators of PI3K/Akt signaling can be used to promote epithelial repair.

Activators

As demonstrated herein activators of PI3K/Akt signaling can be used to increase α5β1 integrin expression and promote epithelial repair. That is, the activation of PI3K/Akt signaling is central to the promotion of epithelial repair.

In some embodiments the activator may also function as a COX-2 inhibitor, for example celecoxib. In other embodiments the activator may lack a COX-2 inhibitory function, for example dimethyl-celecoxib.

Suitable activators may be selected from the group, celecoxib, dimethyl-celecoxib, SC-79 (2-Amino-6-chloro-α-cyano-3-(ethoxycarbonyl)-4H-1-benzopyran-4-acetic acid ethyl ester), Fumosinin B1, IGF-1, urofollitropin, arsenic trioxide, insulin (e.g. human or porcine insulin), insulin derivatives (e.g. NN344, AT1391, crosstide, biotinylated crosstide, insulin receptor substrate (e.g. Tyr608; KKHTDDGYMPMSPGVA), 740 Y-P(PDGFR740Y-P)), SC-58125 (5-(4-fluorophenyl)-1-[4-(methylsulfonyl)phenyl]-3-(trifluoromethyl)-1H-pyrazole), valdecoxib, rofecoxib, 3-trifluoromethyl-5-(p-tolyl)-1H-pyrazole, SC-58236 (4-[5-(4-chlorophenyl)-3-(trifluoromethyl)-1H-pyrazol-1-yl] benzenesulfonamide), sulfanilamide, OSU-03012 (AR-12,2-Amino-N-[4-[5-(2-phenanthrenyl)-3-(trifluoromethyl)-1H-pyrazol-1-yl]phenyl]acetamide), sulfasalazine, parecoxib sodium, piroxicam, NS-398 (N-[2-(Cyclohexyloxy)-4-nitrophenyl]methanesulfonamide), 4-[2-[1-(4-methylphenyl)ethylidene]hydrazinyl] benzenesulfonamide, hydroxy celecoxib, deracoxib, 4-desmethyl-3-methyl celecoxib, N-de(4-sulfonamidophenyl)-N'-(4-sulfonamidophenyl) celecoxib, 2,5-dimethyl-celecoxib, desmethyl celecoxib (CAY10452), celecoxib carboxylic acid, benzenesulfonamide, and SC-560 (5-(4-Chlorophenyl)-1-(4-methoxyphenyl)-3-trifluoromethyl pyrazole).

For example the activator may be selected from SC-58125, valdecoxib, rofecoxib, SC-58236, OSU-03012 (AR-12,2-Amino-N-[4-[5-(2-phenanthrenyl)-3-(trifluoromethyl)-1H-pyrazol-1-yl]phenyl]acetamide), parecoxib sodium, NS-398, hydroxy celecoxib, deracoxib, 4-desmethyl-3-methyl celecoxib, N-de(4-sulfonamidophenyl)-N'-(4-sulfonamidophenyl) celecoxib, 2,5-dimethyl-celecoxib, desmethyl celecoxib (CAY10452), celecoxib carboxylic acid, celecoxib, and SC-560 (5-(4-Chlorophenyl)-1-(4-methoxyphenyl)-3-trifluoromethyl pyrazole).

In one embodiment the activator may be parecoxib sodium, NS-398, or hydroxy celecoxib.

Methods

The present technology relates to methods of promoting repair or regeneration of all types of epithelia, that is the methods promote re-epithelialization. The methods involve administration of an activator to a subject to activate PI3K/Akt signalling and promote epithelium repair.

During the healing of a wound fibroblastic cells are attracted to the wound bed and begin to secrete collagenous ECM known as granulation tissue. Concurrently, epithelial cells from the epidermis neighboring the wound site begin to migrate over the surface of the wound bed until the two epithelial tongues meet, providing a new epithelial coverage. It is only after re-epithelialization that many fibroblastic cells in the granulation tissue undergo programmed cell-death (apoptosis), while others differentiate to fully heal a wound.

There are very few drugs for expediting or improving re-epithelialization or wound healing. Epidermal growth factor, which stimulates the division and migration of keratinocytes in vitro, was considered a therapy with high potential after promising initial clinical results but this promise failed to translate into long-term clinical success. To date, the only growth factor that has reached the clinic is platelet-derived growth factor BB (PDGF-BB), which has received approval for use in treating diabetic foot ulcers.

The methods disclosed herein are applicable to subjects who are undergoing or have undergone a treatment, where the treatment delays or provides ineffective re-epithelialization. Such treatments can include, but are not limited to, medications, radiation, and treatments that result in suppressed immune systems. In other embodiments a subject may have a disease or condition that delays or provides ineffective re-epithelialization. Such diseases or conditions include, but are not limited to asthma, diabetes, peripheral vascular disease, infection, autoimmune disorders, systemic illness which is typically accompanied by chronic or acute inflammation that contributes to epithelial damage, smoking, and stress.

The methods are also applicable to subjects who have a wound, for example a pressure ulcer, a decubitus ulcer, a venous ulcer, a burn, a surgical wound, or other wound.

In an embodiment the invention relates to a method of treatment of a disease or condition associated with reduced PI3K/Akt signaling in a subject, the method comprising administering to the subject an effective amount of an activator of PI3K/Akt signaling or a salt, hydrate, solvate thereof, or a pharmaceutical composition thereof.

In a further embodiment the invention relates to the use of an activator of PI3K/Akt signaling or a salt, hydrate, solvate thereof, or a pharmaceutical composition thereof, in the manufacture of a medicament for treating a disease or condition associated with reduced PI3K/Akt signaling.

In another embodiment the invention relates to a method of treatment of a disease or condition associated with impaired epithelial repair, such as asthma, the method comprising administering to the subject an effective amount of an activator of PI3K/Akt signaling or a salt, hydrate, solvate thereof, or a pharmaceutical composition thereof.

In a further embodiment the invention relates to the use of an activator of PI3K/Akt signaling or a salt, hydrate, solvate thereof, in the manufacture of a medicament for the treatment of a disease or condition associated with impaired epithelial repair, such as asthma.

In another embodiment the present invention relates to the use of an activator of PI3K/Akt signaling or a salt, hydrate, solvate thereof or a pharmaceutical composition thereof for the treatment of a disease or condition associated with reduced PI3K/Akt signaling, or impaired epithelial repair, such as asthma.

The expression "a disease or condition associated with impaired epithelial repair" means that the impaired epithelial repair plays a role in the disease or condition. However, other pathways and mechanisms may also be implicated in the disease or condition.

In an embodiment the subject is a human. In an embodiment the human is a small child or an infant.

In an embodiment the disease or condition is asthma.

The methods described herein are useful for promoting epithelial repair or regeneration in any epithelium. The mammalian body comprises many different types of epithelia, the structures and complexity of which vary depending on their location, role, and function. For example the most basic form of epithelium is the simple epithelium, which comprises a single layer of epithelial cells. An example of a form of simple epithelium is simple squamous epithelium such as the mesothelium, endothelium, and the lining of pulmonary alveoli. Stratified epithelium comprises a series of layers, for example the stratified epithelial layer that covers the skin. Further examples of stratified epithelia include stratified columnar epithelia, and stratified ciliated columnar epithelia, in which the uppermost layer of cells are columnar in shape, and provided with motile cilia.

In another embodiment the invention relates to a method for treating, or inhibiting the progression or development of a disease or disorder in a subject, the method comprising administering to the subject a therapeutically effective amount of an activator of PI3K/Akt signaling or a pharmaceutical composition thereof to promote epithelium repair in the subject Promotion of epithelial repair, regeneration (collectively re-epithelialization), can be described by % acceleration of re-epithelialization. In certain embodiments, the administration of the effective amount of an activator accelerates re-epithelialization by greater than 50%, or equal to or greater than 60%, equal to or greater than 70%, equal to or greater than 75%, equal to or greater than 80%, equal to or greater than 85%, equal to or greater than 90%, equal to or greater than 95%, equal to or greater than 100%, equal to or greater than 110% or more, when compared to a control.

Formulations

The activators of PI3K/Akt signaling described herein may be administered as a composition or formulation comprising a pharmaceutically effective amount of the activator, in association with one or more pharmaceutically acceptable excipients including carriers, vehicles and diluents. The term "excipient" herein means any substance, not itself a therapeutic agent, used as a diluent, adjuvant, or vehicle for delivery of a therapeutic agent to a subject or added to a pharmaceutical composition to improve its handling or storage properties or to permit or facilitate formation of a solid dosage form such as a tablet, capsule, or a solution or suspension suitable for oral, parenteral, intradermal, subcutaneous, or topical application. Excipients can include, by way of illustration and not limitation, diluents, disintegrants, binding agents, adhesives, wetting agents, polymers, lubricants, glidants, stabilizers, and substances added to mask or counteract a disagreeable taste or odor, flavors, dyes, fragrances, and substances added to improve appearance of the composition. Acceptable excipients include (but are not limited to) stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutically acceptable materials. Examples of excipients and their use is described in *Remington's Pharmaceutical Sciences,* 20th Edition (Lippincott Williams & Wilkins, 2000). The choice of excipient will to a large extent depend on factors such as the particular mode of administration, the effect of the excipient on solubility and stability, and the nature of the dosage form.

The activators may be formulated for oral, injectable, parenteral, subcutaneous, intravenous, intranasal, topical, or intramuscular delivery. Non-limiting examples of particular formulation types include tablets, capsules, caplets, powders, granules, injectables, ampoules, inhalers, vials, ready-to-use solutions or suspensions, lyophilized materials, creams, lotions, ointments, gels and drops. Solid formulations such as the tablets or capsules may contain any number of suitable pharmaceutically acceptable excipients or carriers described above. The activators may also be formulated for sustained delivery.

Tablets and capsules for oral administration may be in unit dose presentation form, and may contain conventional excipients such as binding agents, for example, acacia, gelatin, sorbitol, tragacanth, or polyvinylpyrollidone; fillers, for example lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents such as sodium lauryl sulphate. The tablets may be coated according to methods well known in normal pharmaceutical practice.

Liquid preparations may be in the form of, for example, aqueous or oily suspensions, solutions, emulsions, syrups or elixirs, or may be presented as a dry product for reconstitution with water or other suitable vehicle before use. Liquid preparations may be suitable for administration as drops (.e.g. ear drops), nasal sprays, Such liquid preparations may contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, oily esters such as glycerin, propylene glycol, or ethyl alcohol; preservatives, for example, methyl or propyl p-hydroxybenzoate or sorbic acid; and, if desired, conventional flavouring or colouring agents.

For parenteral administration, including intravenous, intramuscular, subcutaneous, or intraperitoneal administration, fluid unit dosage forms may be prepared by combining the compound and a sterile vehicle, typically a sterile aqueous solution which is preferably isotonic with the blood of the recipient. Depending on the vehicle and concentration used, the compound may be either suspended or dissolved in the vehicle or other suitable solvent. In preparing solutions, the compound may be dissolved in water for injection and filter sterilized before filling into a suitable vial or ampoule and sealing. Advantageously, agents such as a local anaesthetic, preservative and buffering agents can be dissolved in the vehicle. To enhance the stability, the composition may be frozen after filling into the vial and the water removed under vacuum. The dry lyophilized powder may then be sealed in the vial and an accompanying vial of water for injection or other suitable liquid may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. A surfactant or wetting agent may be included in the composition to facilitate uniform distribution of the compound.

PI3K/Akt signaling influences a wide variety of human diseases and therapeutic development of AKT inhibitors has been a significant focus of oncology as over 50% of human tumors display hyperactivation of AKT. Accordingly, in some embodiments it may be advantageous to deliver the activator directly to the site where re-epithelisation is required, for example by using an inhaler or a topical application.

Oral Formulations—Inhalers

An activator of PI3K/Akt signaling can be administered orally to a subject. Oral administration be achieved using formulations such as tablets or capsules that are ingested. In other embodiments oral administration is achieved using an inhaler to deliver a metered dose of an activator to a subject. Inhaled activator may be administered as a dry powder or may be delivered using an aerosol inhaler.

Aerosol inhalers are known in the art and commonly utilise an activator together with a suitable carrier. These carriers may be fluorinated materials, such as HFCs (hydrofluorocarbons) and HFAs (hydrofluoroalkanes), which have benefits of low toxicity, inertness, stability and suitable physical properties. Aerosol inhalers are active inhalers in the sense that they generate an aerosol of the activator by means of a propellant, pump, or compressed or liquefied gas.

An alternative to an aerosol inhaler is the use of 'dry-powder' inhalers which deliver the activator as fine particles without the need for a carrier. Dry powder inhalers often use the air stream generated by a user who breathes in and sucks air through the inhaler to entrain a dry powder comprising a drug. Dry-powder inhalers are known in the art and typically comprise a micronized drug. In some embodiments dry powder inhalers The activators disclosed herein can be provided in the form of particles (for dry powder or aerosol inhalers) having a diameter (for example a mean particle diameter) less than about 10 microns, or less than about 9, 8, 7, 6, 5, 4, 3, 2 or 1 micron. Particles of greater than about 10 microns commonly are trapped in the mouth and throat when inhaled, and are therefore not effectively delivered to the lungs. Particles below about 0.5 microns appear to have reduced deposition in the lungs, and are therefore not effectively absorbed by a subject. Particles of an activator have a diameter between about 0.5 and about 10 microns, and may have a particle diameter of between about 0.5 and 5, 0.5 and 1, 1 and 10, 5 and 10 or 1 and 5 microns, and may have a particle diameter of about 0.5, 1, 1.5, 2, 2.5, 3, 3.5, 4, 4.5, 5, 5.5, 6, 6.5, 7, 7.5, 8, 8.5, 9, 9.5 or 10 microns. The proportion of particles of the inhalable drug less than 10 microns (or less than 9, 8, 7, 6, 5, 4, 3, 2 or 1 microns) in diameter, or between 0.5 and 10 microns in diameter may be greater than about 50%, or greater than about 60, 70, 80, 90 or 95%, on a weight basis, and may be about 50, 55, 60, 65, 70, 75, 80, 85, 90, 95, 96, 97, 98 or 99%. The particles of the inhalable drug may have a narrow particle size distribution. The proportion of particles of the inhalable drug having a particle size within 10% (or 15, 20, 25, 30, 35, 40, 45 or 50%) of the mean particle size may be greater than about 20%, or greater than about 30, 40, 50, 60, 70, 80 or 90% on a weight basis, and may be about 20, 30, 35, 40, 45, 50, 55, 60, 65, 70, 75, 80, 85, 90, 95, 96, 97, 98 or 99% on a number or weight basis Topical Formulations In some embodiments the activator is provided in the form of a wound dressing, ointment or cream. For example the activator is provided in the form of a liquid, semi-solid or solid composition for application directly to the surface of a wound, or the composition is applied to the surface of, or incorporated into, a solid wound contacting layer such as a wound dressing gauze or film. The wound dressing composition may be provided in the form of a fluid or a gel. The activator may be provided in combination with conventional pharmaceutical excipients for topical application to a wound. Suitable carriers include: Hydrogels containing cellulose derivatives, including hydroxyethyl cellulose, hydroxymethyl cellulose, carboxymethyl cellulose, hydroxypropylmethyl cellulose and mixtures thereof, and hydrogels containing polyacrylic acid (Carbopols). Suitable carriers also include creams/ointments used for topical pharmaceutical preparations, e.g. creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilisers such as EDTA.

In one embodiment of the invention, the wound dressing composition may be a slow release solid composition, in which the at least one activator is dispersed in a slow release solid matrix such as a matrix of alginate, collagen, or a synthetic bioaborbable polymer. In an embodiment the wound dressing composition is a sterile dressing.

The term "wound dressing" refers to a dressing for topical application to a wound and excludes compositions suitable for systemic administration. For example, the activator may be dispersed in or on a solid sheet of wound contacting material such as a woven or nonwoven textile material, or may be dispersed in a layer of foam such as polyurethane foam, or in a hydrogel such as a polyurethane hydrogel, a polyacrylate hydrogel, gelatin, carboxymethyl cellulose, pectin, alginate, and/or hyaluronic acid hydrogel, for example in a gel or ointment. In an embodiment the activator may be dispersed in or on a biodegradable sheet material that provides sustained release of the active ingredient into the wound, for example a sheet of freeze-dried collagen, freeze-dried collagen/alginate mixtures.

In some embodiments an activator may be administered as a topical formulation. In addition to the activator, a topical formulation may comprise one or more carriers and excipients, including viscosity increasing agents, ointment bases (e.g., cream bases), antimicrobial preservatives, emulsifying agents, and/or solvents.

A "viscosity increasing agent" is an agent that is used to thicken a formulation. Exemplary viscosity increasing agents may include, for example, cetostearyl alcohol, cholesterol, stearyl alcohol, chlorocresol, white wax, stearic acid, cetyl alcohol, or a combination thereof. The viscosity increasing agent may be present in the topical formation at a concentration of about 1.0-10% (w/w). For example, the topical formulation may comprise about 1-1.5%, 1.5-2%, 2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9-9.5%, or 9.5-10% (w/w) of the viscosity increasing agent. Alternatively, the topical formulation may comprise about 1-5%, 2.5-7.5%, or 5-10% (w/w) of the viscosity increasing agent.

An "ointment base" can be any semisolid preparation or vehicle into which an active agent may be incorporated. Exemplary ointment bases include, but are not limited to, oleaginous ointment bases (e.g., white petrolatum or white ointment), absorption ointment bases (e.g., hydrophilic petrolatum, anhydrous lanolin, Aquabase™, Aquaphor®, and Polysorb®), water/oil emulsion ointment bases (e.g., cold cream, hydrous lanolin, rose water ointment, Hydrocream™, Eucerin®, and Nivea®), oil/water emulsion ointment bases (e.g., hydrophilic ointments, Dermabase™, Velvachol®, and Unibase®), and water-miscible ointment bases (e.g., polyethylene glycol (PEG) ointment and Polybase™). Ointment bases may be pharmacologically inert but can entrap water in order to provide an emollient protective film. In a specific embodiment, the ointment base may be any petrolatum compound (e.g., petrolatum, white petrolatum, white soft paraffin, liquid petrolatum, liquid paraffin). In a further specific embodiment, the ointment base is white petrolatum (CAS number 8009-03-8). The ointment base may be present in the topical formation at a concentration of about 5-30% (w/w), e.g., 10-30% (w/w). For example, the topical formulation may comprise about 5-25%, 5-20%, 5-15%, 5-15%, 10-15%, 15-20%, 20-25%, or 25-30% (w/w) of the ointment base. Specifically, the topical formulation may comprise about 5, 6, 7, 8, 9, 10, 11, 12, 13, 14, 15, 16, 17, 18, 19, 20, 21, 22, 23, 24, 25, 26, 27, 28, 29, or 30 percent (w/w) of the ointment base.

In some embodiments, the "ointment base" contains less than 20% water and volatiles, and more than 50% hydrocarbons, waxes, or polyols as the vehicle. In some embodiments, the "ointment base" described herein is a "cream base," which contains more than 20% water and volatiles and/or typically contain less than 50% hydrocarbons, waxes, or polyols as the vehicle for the drug substance. The cream base can be a multiphase preparation containing a lipophilic phase and an aqueous phase. In some instances, the cream base is a lipophilic cream base, which has a lipophilic phase as the continuous phase. Such a cream base usually contains water-in-oil emulsifying agents such as wool alcohols, sorbitan esters and monoglycerides. In other instances, the cream base is a hydrophilic cream base, which has an aqueous phase as the continuous phase. Such a cream base typically contains oil-in-water emulsifying agents such as sodium or trolamine soaps, sulfated fatty alcohols, polysorbates and polyoxyl fatty acid and fatty alcohol esters, which may be in combination with water-in-oil emulsifying agents, if needed.

An "antimicrobial preservative" refers to any compound capable of destroying microbes, preventing the multiplication or growth of microbes, or preventing the pathogenic action of microbes. Exemplary antimicrobial preservatives include, but are not limited to, a paraben compound (an ester of para-hydroxybenzoic acid; e.g., paraben, methylparaben, ethylparaben, propylparaben, butylparaben, heptylparaben, benzylparaben, isobutylparaben, isopropylparaben, benzylparaben, or their sodium salts), benzalkonium chloride, benzethonium chloride, benzyl alcohol, boric acid, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

An "emulsifying agent" is a compound or substance which acts as a stabilizer for a mixture of two or more liquids that are normally immiscible (unmixable or unblendable). Exemplary emulsifying agents may include, but are not limited to, natural emulsifying agents (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, propylene glycol monostearate, and polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, and methylcellulose), sorbitan fatty acid esters (e.g., polyoxyethylene sorbitan monolaurate [Tween® 20], polyoxyethylene sorbitan [Tween®60], polyoxyethylene sorbitan monooleate [Tween® 80], sorbitan monopalmitate [Span® 40], sorbitan monostearate [Span® 60], sorbitan tristearate [Span® 65], glyceryl monooleate, and sorbitan monooleate [Span® 80]), polyoxyethylene esters (e.g., polyoxyethylene monostearate [Myrj® 45], polyoxyethylene hydrogenated castor oil, polyethoxylated castor oil, polyoxymethylene stearate, and Solutol), sucrose fatty acid esters, polyethylene glycol fatty acid esters (e.g., Cremophor®), polyoxyethylene ethers (e.g., polyoxyethylene lauryl ether [Brij® 30]), and poly(vinylpyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, and docusate sodium, and/or combinations thereof. The emulsifying agent may be present in the topical formation at a concentration of about 0.5-10% (w/w), e.g., 0.5-6% (w/w). For example, the topical formulation may comprise about 0.5-1%, 1-1.5%, 1.5-2%, 2-2.5%, 2.5-3%, 3-3.5%, 3.5-4%, 4-4.5%, 4.5-5%, 5-5.5%, 5.5-6%, 5-10%, 6-10%, or 8-10% (w/w) of the emulsifying agent. Specifically, the topical formulation may comprise about 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 percent (w/w) of the emulsifying agent.

Topical formulations may further contain one or more solvents (e.g., non-water solvents or water). Exemplary non-water solvents may include, but are not limited to, any known solvent including propylene glycol, glycol, and mixtures thereof. The non-water solvent may be present in the topical formation at a concentration of about 2-65% (w/w). For example, the topical formulation may comprise about 2-15%, 15-30%, 30-45%, or 45-65% (w/w) of the solvent. In some embodiments, the topical formulation may also contain water.

In some embodiments, a topical formulation may further comprise one or more emollients, fragrances, or pigments. The topical formulation may also be used in conjunction with a wound dressing (e.g., bandage with adhesive, plaster patch and the like).

Ear Drops

In some embodiments the activator is provided in the form of an ear drop. For example the activator is provided in the form of a liquid, or gel for application directly into the ear canal such that it can contact the eardrum, for example in the treatment of a perforated eardrum.

In some embodiments the ear drops may contain a substance which allows permeabilization of the activator into and/or across the across the ear drum. Substances which may be used to permeabilize the ear drum include, but are not limited to dimethylsulfoxide (DMSO), dimethylacetamide, methyldecyl sulfoxide, cotton seed oil, caster oil derivatives, fatty acid esters, glycerol, vesicles, liposomes, and anionic surfactants.

Dose

The amount of an activator and the dosage regimen for treating a disease condition with the activator and/or pharmaceutical formulations disclosed herein depends on a variety of factors, including the age, weight, sex, and medical condition of the subject, the severity of the disease or condition, the route and frequency of administration, the particular compound employed, as well as the pharmacokinetic properties (e.g., adsorption, distribution, metabolism, excretion) of the individual treated, and thus may vary widely. Such treatments may be administered as often as necessary and for the period of time judged necessary by the treating physician. One of skill in the art will appreciate that the dosage regime or therapeutically effective amount of the activator to be administrated may need to be optimized for each individual. The pharmaceutical formulations may contain an activator in the range of about 0.1 mg to 2000 mg, for example 10 mg, 20 mg, 30 mg, 40 mg, 50 mg, 60 mg, 70 mg, 80 mg, 90 mg, 100 mg, 200 mg, 300 mg, 400 mg, 500 mg, 600 mg, 700 mg, 800 mg. 900 mg, 1000 mg, 1100 mg, 1200 mg, 1300 mg, 1400 mg, 1500 mg, 1600 mg, 1700 mg, 1800 mg, 1900 mg or 2000 mg. A daily dose of about 0.01 mg/kg to 500 mg/kg body weight, typically between about 0.1 mg/kg and about 50 mg/kg body weight, may be appropriate, depending on the route and frequency of administration. The daily dose will typically be administered in one or multiple, e.g., two, three or four, doses per day.

For example, in embodiments where the activator is celecoxib the dosage may be 10 mg, 50 mg, 100 mg, 200 mg, 300 mg, 400 mg or 500 mg once or twice daily. 200 mg once daily or 100 mg twice daily.

In other embodiments the dosage of the activator (e.g. celecoxib or dimethyl-celecoxib) is sufficient to achieve a plasma concentration of 0.01 µM to at least 10 µM.

Combination Regimens

One or more additional agents that promote repair of epithelium (e.g. growth factors, peptides, proteolytic inhibitors, extracellular matrix components, fragments and peptides, steroids, cytokines, oxygen donators or vitamins) may also be used in the methods and formulations disclosed herein. The additional agents may be administered separately, simultaneously or sequentially with the activator.

In some embodiments one or more additional agents that are known to treat asthma may also be used in the formulations disclosed herein, particularly the inhaled and oral formulations. Suitable asthma therapeutics include for example an inhaled corticosteroid, long-acting bronchodilator (beta-agonists and anticholinergics), theophylline, leukotriene modifiers, an anti-immunoglobulin E (IgE) antibody (e.g. omalizumab), short-acting bronchodilators, systemic corticosteroids, and ipratropium. Such agents may also be used in the methods disclosed herein. The additional agents may be administered separately, simultaneously or sequentially with the activator.

In one embodiment an effective dose of the activator may delivered in conjunction with or alternating with at least one additional agent.

In one embodiment the activator and the additional agent may be administered in a single formulation which comprises both the activator and the additional agent.

In another embodiment the activator and the additional agent are administered separately.

EXAMPLES

Example 1: Materials and Methods

Reagents

Bovine serum albumin, foetal bovine serum, bovine hypothalamus acetone power, hydrocortisone, recombinant human epidermal growth factor, epinephrine hydrochloride, fibronectin, triiodothyronine, transferrin, trans retinoic acid, trypsin, gentamicin, wortmannin solution and SC79 were obtained from Sigma. Bronchial epithelial basal medium (BEBM™) and bronchial epithelial cell growth medium (BEGM™) were purchased from LONZA. Penicillin G, RPMI-1640 media, streptomycin sulfate, amphotericin B and L-glutamine were purchased from Invitrogen. Ultroser G was supplied from Ciphergen. Collagen type I and FN were purchased from BD and all tissue culture plastic ware were purchased from Corning.

Patients and Sample Collection

Two cohorts were used in this study: 55 children with mild asthma, who did not previously receive any corticosteroid therapy, and 117 children with no history of asthma (Table 1). Subjects were between 1.2 and 17.7 years of age, were undergoing elective surgery for non-respiratory related conditions and had no pre-existing bacterial or viral chest infection at the time of recruitment. Children with an existing bacterial or viral chest infection were excluded. Asthma was defined as physician-diagnosed based upon physician documented wheezing episodes in the 12 months preceding their recruitment and confirmed by positive responses on the International Study of Asthma and Allergies in Children (ISAAC) and American Thoracic Society (ATS) respiratory questionnaires All children had mild asthma, such that none are receiving glucocorticosteroids (inhaled or oral) and less than 10% are taking β-agonists. Tracheobronchial AEC were obtained via trans-laryngeal, non-bronchoscopic brushings of children through an endotracheal tube. The study was approved by both Princess Margaret Hospital for Children and St John of God Hospital's Human Ethics Committee and written consent is obtained from each participant's legal guardian after being fully informed about the nature and purpose of the study. All experiments were performed in accordance with the relevant committees' guidelines and regulations.

TABLE 1

Complete patient demographics

| Phenotype | Gender | Mean age (SD; years) | Age range (min-max; years) | Number | Total (n) |
|---|---|---|---|---|---|
| Non-asthmatic | M | 5.6 (3.3) | 1.7-15.6 | 72 | 117 |
| | F | 6.2 (4.1) | 1.2-17.7 | 45 | |
| Asthmatic | M | 6.5 (3.8) | 2.5-16.9 | 40 | 55 |
| | F | 7.2 (4.0) | 2.1-15.4 | 15 | |

Cell Culture

Two different culture methods were used to expand ex vivo human primary airway epithelial cells; traditional BEGM (*Am J Respir Crit Care Med.* 2006; 174(10):1110-8; and *Respir Res.* 2005; 6:53) and the conditional reprogramming method (*Am J Pathol.* 2012; 180(2): 599-607). The remainder of ex vivo cells were used for RNA and/or establishing a traditional BEGM primary cell culture.

Cell Viability Assay

Cell viability was assessed using a 3-[4,5-dimethylthiazol-2yl]-5-[3-carboxymethoxyphenyl]-2-[4-sulfophenyl]-2H-tetrazolium inner salt (MTS) assay (Promega).

Gene Expression Analysis

The mRNA expression of FN-binding integrin subunits and housekeeping gene, PPIA, was determined by using gene specific primers (see Table 2). Gene expression was determined via two-step RT-PCR reactions. Relative gene expression was calculated using the $2^{-\Delta\Delta C_T}$ method by normalization to PPIA housekeeping gene and an endogenous tissue control.

TABLE 2

Details of reference and target genes.
List of all TaqMan primer/probe sets
used in a TaqMan-based qPCR.

| Gene symbol | Gene name(s) | Taqman Assay ID | Amplicon length (bp) |
|---|---|---|---|
| PPIA* | Peptidylprolyl isomerase A (cyclophilin A) | Hs99999904_m1 | 98 |
| ITGAV | Integrin, alpha V | Hs00233808_m1 | 64 |
| ITGA3 | Integrin, alpha 3 | Hs00233722_m1 | 69 |
| ITGA5 | Integrin, alpha 5 | Hs01547673_m1 | 54 |
| ITGB1 | Integrin, beta 1 | Hs00559595_m1 | 75 |
| ITGB3 | Integrin, beta 3 | Hs01001469_m1 | 59 |
| ITGB6 | Integrin, beta 6 | Hs00168458_m1 | 101 |

*Reference gene.

In-Cell™ and On Cell™ Western Assay

Cells were plated at $1.2 \times 10^5$ cells/cm$^2$ onto 96-well plates precoated with fibronectin (10 mM) and maintained as described earlier. Briefly, following relevant treatments and controls, confluent cell monolayers were fixed with 10% (v/v) NBF for 20 minutes at room temperature and then either permeabilized with 0.1% (v/v) Triton X-100 or incubated with PBS for 25 minutes. Cells were blocked for 90 min at room temperature with the Odyssey® blocking buffer (PBS) (LI-COR Biosciences). Cells were then stained with rabbit anti-human integrin α5 (1:100; clone EPR7854, Abcam), mouse anti-human integrin β1 (1:1000; clone P5D2, Abcam), rabbit anti-human phospho-Akt (Ser473) (1:100; clone D9E, Abcam) or mouse anti-human total Akt (pan) (1:100; clone 40D4, Abcam) for 24 hours at 4° C. Antibody binding was determined using IRDye 800 CW-conjugated goat anti-rabbit IgG (1:800; 925-32211, LI-COR Biosciences) and goat anti-mouse IgG (1:800; 925-32210, LI-COR Biosciences), as well as DRAQ5 (1:10000; DR50200, BioStatus Limited) and Sapphire700 (1:1000; 928-40022, LI-COR Biosciences) for cell number normalization, for 1 hour at RT with gentle shaking in the dark. Specific antibody staining for protein expression was then immediately visualized and quantified using an infrared imaging system (LI-COR Biosciences).

On Cell Western™ Assay

After this, cells were washed in 1× phosphate-buffered saline (PBS) and incubated with IRDye-conjugated secondary antibody (1:800 goat anti-rabbit and goat anti-mouse IgG, LI-COR Biosciences, Lincoln, Nebr., USA) containing DRAQ5 (1:10000, BioStatus Limited, Shepshed, United Kingdom) and Sapphire700 (1:1000, LI-COR Biosciences, Lincoln, Nebr., USA) for 1 hour at RT with gentle shaking in a dark room. Cells were then washed for an additional five times in PBS. Specific antibody staining for protein expression was then immediately visualized using an infrared imaging system (LI-COR Biosciences, Lincoln, Nebr., USA Immunocytochemistry and Microscopy For protein expression and localization analysis of integrins in cultured pAEC, fluorescent immunocytochemistry was utilized. Primary AEC of non-asthmatic and asthmatic children were cultured onto FN-coated glass slides to confluence, scratch wounded with sterile p300 pipette tip and 24 hours post wounding fixed with 10% (v/v) NBF for 20 minutes at room temperature. Cells were blocked using Zuk's blocking buffer for 1 hour at room temperature. Then, cells were stained with rabbit anti-human integrin α5 (1:100; clone EPR7854, Abcam), and mouse anti-human integrin β1 (1:1000; clone P5D2, Abcam) for 1 hour at room temperature followed by incubation with secondary antibodies Alexa Fluor® 568 goat anti-rabbit IgG (1:200; Molecular Probes) and Alexa Fluor® 488 goat anti-mouse IgG (1:200; Molecular Probes) for 1 hour at room temperature. Samples were counterstained with nuclear stain, Hoechst 33342 (2.5 µg/mL; Sigma-Aldrich), as indicated in the online supplement. Stained pAEC were acquired using a Nikon® A1 inverted confocal microscope (Nikon), and processed using Nikon Instrument Software (NIS) Elements-Advanced Research (AR) (v4.2.22; Nikon) and ImageJ software.

For imaging of cultured pAEC post wounding, cells were cultured on 0.8 cm round glass coverslips that were pre-coated with FN coating buffer. Cells were then fixed using 10% (v/v) NBF for 15 minutes at room temperature and washed three times for 5 minutes per wash with 1×PBS. The cells were stored in 1×PBS at 4° C. until further required. For immunocytochemical staining for integrin α5 and β1 expression patterns, cultured pAEC were equilibrated to room temperature and incubated with Zuk's blocking buffer for 1 h at room temperature. Following blocking, primary antibodies against human integrin subunits α5 and β1 diluted in Zuk's blocking buffer were incubated onto the glass coverslips overnight at 4° C. The next day, cells were washed 3×5 minutes with 1×PBS. Cells were incubated with AF-conjugated secondary antibodies diluted in Zuk's blocking buffer for 1 h at room temperature. Finally, the cells were washed 3×5 minutes with 1×PBS. Hoechst counterstain was used as a nuclear marker in all confocal fluorescence images. The coverslips were mounted onto glass slides with antifade fluorescence mounting media (DAKO, Glostrup, Hovedstaden, Denmark), edges were sealed and dried prior to imaging. Cultured pAEC were acquired using a Nikon® A1 inverted confocal microscope (Nikon, Minato, Tokyo, Japan), with a Nikon® Plan Apo VC 60× Numerical Aperture (NA) 1.4 oil immersion objective (Nikon, Minato, Tokyo, Japan) and processed with Nikon Instrument Software (NIS) Elements-Advanced Research (AR) (v4.2.22; Nikon, Minato, Tokyo, Japan) and ImageJ software. Individual channels were captured sequentially, where a 405 nm laser was used for Hoechst 33342 with collection through a 450/50 bandpass filter, AF488 excited using a 488 nm laser with collection through 525/50, and AF568 excited with a 561 nm laser and collected through a 585/50 bandpass filter. Z-stack images with step size of 0.5 µm were collected with a pinhole of 35.8 µm (1.2 AU for 488 nm laser), where the top and bottom of the stacks were determined visually.

Example 2: Wound Repair Assays 96-well Essen Woundmaker

Two in vitro scratch wound models were used. To assess wound repair kinetics, linear scratch wounds were created using a commercial monolayer wounding kit (*Nature*. 2013; 495(7439): 103-6). Wound closure was calculated through image analysis by the accompanying live-cell imaging system (Essen Bioscience, Ann Arbor, Mich., USA).

Pipette Tip Scratch Wounding

To isolate leading edge cells for RNA-Sequencing data analysis, small scratch wounds were made using a plastic p300 pipette tip as previously described (*Clinical and Experimental Allergy*. 2008; 38(12): 1901-1910).

Leading Edge Cell Tracking

Manual Tracking, an ImageJ2 plugin publicly available was utilized for its capacity to manually track cells in two dimensions, the x and y planes. Time-lapse images of the first 12 h post wounding were loaded into ImageJ2 and 10-20 individual leading edge cells were arbitrarily selected from both wound margins, that is, top and bottom margins.

The selected cells were tracked over the first 12 h post wounding, where this procedure generated x and y coordinates for the position of the nucleus of each tracked cell at each time point. The x,y coordinates of the tracked cells were exported in a tab delimited format and all tracks were transformed to migrate up towards the y-axis.

Data Interpretation and Quantification of Migration Parameters

Graphical representation and analysis of the cell migration parameters was performed using the Chemotaxis and Migration Tool 2.0 (Ibidi®, Martinsried, Bayern, Germany). The x,y coordinates were imported into the Chemotaxis and Migration Tool 2.0, where the x,y coordinates of cell tracks were transformed to a common origin (0,0) for downstream data analysis and visualization purposes. Data was graphically presented in various forms, including 2D trajectory plots where the origin represented the wound margin and the trajectories indicated the migration paths of individual cells over 12 hours. In addition, circular plots were used to indicate the directional frequency of tracks at each angle position, with the maxima of counts, marked in red. Migration parameters of cell tracks were then quantified including; (1) distance migrated (µm) which represented the displacement of a cell from the start to its endpoint, (2) velocity (µm/min), which is a function of displacement overtime, and (3) directionality (AU), which represents a measurement of the directness or straightness of a cell trajectory and was calculated as a ratio of the cell displacement over the accumulated distance migrated. A ratio of 1 indicated absolute directional cell migration and a ratio of 0 indicated totally random migration. Since directionality is not a direct measure of chemotaxis, the determined forward migration index (FMI) (AU) was then utilized to represent the efficiency of the leading edge cells to migrate towards the center of the wounded area. Since leading edge cells were expected to move forward towards the center of the wound, FMI along the y-axis (yFMI) was reported. yFMI was calculated as a ratio of the y-coordinate at the cell endpoint over displacement, where a high determined value indicated a high efficiency of leading edge cells to respond to the generated wound.

Leading Edge Cell Isolation

Submerged pAEC cultures were grown on FN-precoated 12-well plates until 100% confluence was achieved. Once completely confluent, cell monolayer cultures were incubated in wounding media for 24 hours and subsequently scratch wounded as previously described (refer to 2.5.3.1). Plates were then washed using wounding media to remove any cellular debris. Wounded cultures were incubated at 37° C. over a 24-hour period. Cells lining the leading edge of the wound were collected immediately after wounding (time 0 h) and 24 hours later. Cells distal to the wound site were also collected as an internal control at both time points. Leading edge cells were detached from the cell monolayer by scraping behind the first 3 rows of cells from the wound edge using a p200 Gilson pipette tip under stereomicroscopic guidance (modular stereomicroscope Leica MZ6, Leica Microsystems, Wetzlar, Hesse, Germany) and sterile conditions. Leading edge cells were pooled from two wells to collect sufficient cells and RNA for downstream analyses. Similarly, cells from distal sites to the wound were pooled from two wells to collect sufficient cells and RNA. Isolated cells were collected in BEBM, centrifuged at 700 g for 3 minutes at 4° C. to form a cell pellet. Cells were lysed in QIAzol lysis buffer, snap frozen in liquid nitrogen and stored at −80° C. until all samples were collected and extracted to minimize any potential multi-batch variance.

Example 3: RNA Isolation and RNA Sequencing

RNA Extraction and cDNA Library Preparation for RNA-Seq

Total RNA was extracted using QIAzol lysis buffer and the miRNeasy micro kit (QIAGEN) according to manufacturer's instructions. Following extraction, total RNA purity, yield, and integrity was determined via NanoDrop spectrophotometer, Qubit fluorometer and Agilent 2100 Bioanalyser respectively. Samples containing at least 500 ng of total RNA of high purity (A260/280>2.0) and quality (RIN>7.5) were processed for library preparation.

For RNA-Seq analysis, the KAPA Stranded mRNA-Seq kit (KAPA Biosystems Basel, Basel-Stadt, Switzerland) was used for mRNA capture and fragmentation into 200-300 bp fragments. RNA libraries were created from each sample s using KAPA Stranded mRNA-Seq library preparation kit (KAPA Biosystems (Roche),) following the company recommended protocol.

RNA fragments were subsequently reverse transcribed into cDNA strands, which was followed by adapter ligation and library amplification for single-end read sequencing. The quality and quantity of all libraries were assessed using Agilent Bioanalyser and Qubit respectively. Sample libraries were sequenced on the Illumina® HiSeq 2500 platform at a sequence length of 100 bp and depth of about >3 million reads per sample stored in the fastq file format. The quality and quantity of all libraries were assessed using Agilent Bioanalyser and Qubit respectively. Sample libraries were sequenced on the Illumina® HiSeq 2500 platform at a sequence length of 100 bp and depth of about >3 million reads per sample stored in the fastq file format. The sequence reads were assessed for quality and quantity using FastQC (http://www.bioinformatics.babraham.ac.uk/projects/fastqc).

RNA-Seq and Transcriptomic Analysis

RNA-Seq was performed on an Illumina GA IIx instrument using single end reads followed by de-multiplexing using CASAVA. Sequencing quality was assessed based on GC content, average base quality and Illumina adapter contamination using FastQC. Reads were mapped to the human genome (GRCh37—Ensembl) using Tophat2, sorted and indexed using Samtools and counted using HTseq. To establish a signature gene expression profile from pAEC isolates (i.e. leading edge and distal site samples at times 0 and 24 hours post wounding) from children with or without asthma, DESeq2 was used to identify genes that had statistically significant differential expression (Benjamini-Hochberg-adjusted p-value<0.050, fold change cut off of 1.5) in two comparisons: between asthmatic distal 0 h and non-asthmatic distal 0 h, and between asthmatic leading edge 24 hours and non-asthmatic leading edge 24 hours.

Pathway and gene ontology analyses were performed on these signature gene expression profiles using InnateDB (*Nucleic Acids Res.* 2013; 41(Database issue): D1228-33.) to identify unique pathways and gene ontologies based on over-representation of genes. Network analysis of expression changes were performed using NetworkAnalyst (*Nat Protoc.* 2015; 10(6): 823-44 and *Nucl Acids Res.* 2014; 42(W1): W167-74.) which is based on curated protein: protein interactions from InnateDB. Ingenuity® Pathway Analysis (IPA®, QIAGEN Redwood City, Calif., USA) was used to identify upstream transcriptional regulators of the differentially expressed genes. Positive z-scores (z-scores>2) indicate activation and negative z-scores (z-scores s≤−2) indicate inhibition of the upstream regulator and adjusted p-values<0.050 were considered significant as recommended by IPA®.

Statistics

Before statistical evaluation, all results were tested for population normality and homogeneity of variance. Experiments were performed in at least duplicates. Two-group comparisons of parametric data was analyzed using a Student's t-test. For all two-group comparisons of non-parametric data, analysis was performed using a Mann-Whitney test. For statistical analyses involving three groups or more, One-way analysis of variance and Dunnett's test were performed. Experiments were performed at least in triplicate and using at least four patients of each cohort per experiment. Values are presented as mean±SD. All p values less than 0.050 were considered to be significant.

Example 4: Data Processing

A metadata table was constructed containing all clinical and sample-specific information. Subsequently, the single-end sequence reads were mapped to the reference genome (*Homo sapiens* GRCh37—Ensembl) using 'TopHat2'. The mapped reads were then transformed from a BAM file, which is a binary sequence alignment/map file, into the sorted and indexed version, SAM, a tab-delimited text file that contains sequence alignment/map data, with 'samtools'. The mapped reads were inspected using the integrative genomics viewer (IGV). The count reads were then added to the metadata table using 'htseq-count'. DESeq2 was used to transform count reads by invoking a variance-stabilizing transformation and sample variance was inspected with principal component analysis (PCA) and volcano plots. Differential gene expression was determined as having a fold change of more than 1.5 (upregulated) and less than −1.5 (downregulated) compared to control with a p-value adjusted for multiple testing using the Benjamini-Hochberg procedure (Benjamini-Hochberg-adjusted p-value<0.050).

Differential Gene Expression Analysis

Various online open-source platforms such as InnateDB (*Nucleic Acids Res.* 2013; 41(Database issue): D1228-33.) and NetworkAnalyst (Nat Protoc. 2015; 10(6): 823-44 and Nucl Acids Res. 2014; 42(W1): W167-74) were used to facilitate systems-level analyses by enabling the integration, analysis and visualization of gene expression data, in the context of molecular interaction networks and canonical pathways. Several statistical and analytical tools have been integrated into InnateDB, which were used to rapidly determine canonical pathways, as well as biological processes, cellular component and molecular function (represented by Gene Ontology analysis) that were statistically overrepresented in the transcriptomic experiments of interest. InnateDB is the largest database of interactions curated with respect to genes involved in host responses and provides a major advantage in permitting the creation of substantially enriched networks relevant to integrins, cell migration, and wound repair.

Ingenuity® Pathway Analysis (IPA®, QIAGEN Redwood City, Calif., USA, was used to identify Upstream Regulator Analysis. Upstream Regulator Analysis is a predictive causal analysis identifying upstream molecules or networks of molecular drivers, including transcription factors and endogenous chemicals that may be regulating the observed transcriptional differences in the datasets. Specifically, this analysis compares the overlap between known downstream targets of each transcriptional regulator with the differentially expressed (DE) gene lists, and is thus statistically predicted to identify molecules regulating the observed differential expression pattern. Also, IPA® predicts whether the transcriptional regulators are activated or inhibited, based on known relationships between each regulator and the expression (up- or down-regulation) of the downstream targets within each dataset. These predictions are reported as activation z-scores, and are a second method for ranking predicted upstream transcriptional regulators after the adjusted p-values. Positive z-scores indicate activation and negative z-scores indicate inhibition of the upstream regulator. Absolute activation z-scores>2 and adjusted p-values<0.050 were considered significant as recommended by IPA®.

Data Analyses and Presentation

Hierarchical Clustering

Hierarchical clustering was performed to ensure sample dissimilarity based on transcriptional expression patterns irrespective of experimental parameters including: clinical diagnosis of asthma, when samples were collected post wounding (0 and 24 hours), and location where samples were collected (leading edge (lead) and sites distal to the wound (distal)).

Heatmap

A gradient of heterogeneity was performed to illustrate sample heterogeneity. In schematic format, it is colour coded in the sample-to-sample distance heatmap where blue colour indicates strong sample homogeneity and darker shades of red colour indicate increasing sample heterogeneity.

Volcano Plots

A volcano plot was constructed to quickly identify any changes in large data sets. The volcano plot represents each gene with a dot, where on the x-axis is their log 2 fold change between two conditions, and on the y-axis the negative log 10 of p-value. Genes with a Benjamini-Hochberg-adjusted p-value<0.050 are shown typically in an orange colour.

Gene Network Maps

Network maps were utilized to understand and visualize the collective functions of differentially genes, as well as the relationships among them, particularly any non-obvious relationships. In this study, to analyze and visualize interactions between human genes, NetworkAnalyst was used. NetworkAnalyst uses a comprehensive high-quality protein-protein interaction database downloaded from InnateDB, where the database was created by manually curating protein interaction data from published literature as well as by integrating experimental data from various databases (Nucl Acids Res. 2014; 42(W1): W167-74). To date, the database contains 14,755 proteins and 145,955 experimentally confirmed interactions for humans.

Topology analysis was also performed since it considers the whole network structure and was used to search for important gene interaction nodes. In particular, gene interaction nodes that were the most highly interconnected, also known as hubs were identified. It is, generally, accepted that changes in the hubs of a network would have more impact on the network than changes on marginal or relatively isolated nodes. Therefore, NetworkAnalyst provides two well-established node centrality measures to estimate node importance—hub degree centrality and betweenness centrality. In a graph network, the hub degree of a node is the number of connections it has to other nodes. The betweenness centrality measures the number of shortest paths going through the node and it takes into consideration the global network structure. For example, nodes that occur between two dense clusters have a high betweenness centrality even if their degree centrality values are not high.

Example 5: Results

Defective Cell Migration as a Mechanism of Dysregulated Asthmatic Airway Epithelial Repair Pediatric pAEC cultures from non-asthmatic children typically demonstrate a rapid wound repair response where cultures reach wound closure of 89.92±12.32% within 48 h post wounding and complete wound closure by 60 h post wounding on average (FIG. 1A). However, pAEC cultures of children with asthma displayed a significantly lower wound closure of 35.28±20.39% by 48 h post wounding (p<0.010) and failed to close the wound over the course of the scratch assay (FIG. 1B).

Figure 2:
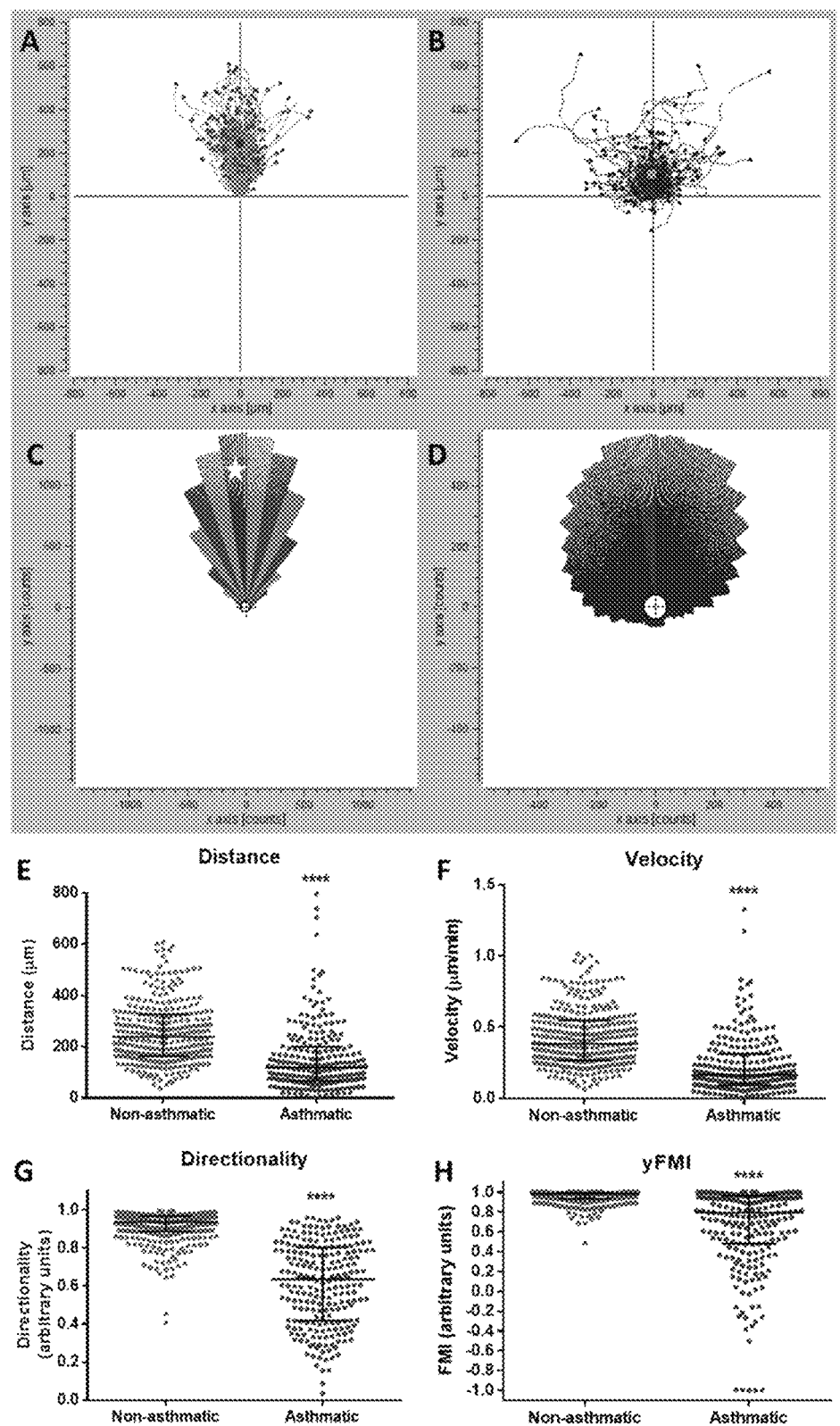
FIG. 2: Defective cell migration of leading edge cells in cultures of children with asthma. Monolayer pAEC cultures from non-asthmatic and asthmatic children were scratch wounded and leading edge pAEC migration was determined using time-lapse imaging at 30-minute intervals during the first 10 h of wound repair. (A-B) Cell migration trajectory plots showing the individual tracks of leading edge pAEC from non-asthmatic (A) and asthmatic (B) children migrating over 10 h post scratch wounding, where individual tracks were transposed so that each had its start at the origin. (A, C) Leading edge pAEC of non-asthmatic children responded to the scratch wounding stimulus by migrating directionally, towards the center of the wound site. Individual tracks were transposed so that each had its start at the origin. (B, D) Leading edge pAEC of asthmatic children showed a dysregulated response to wounding where some cells migrated into the wound site in a random manner and other cells did not migrate very far into the wound and even migrated backwards into the leading edge. The dots represents the mean center of mass of the endpoints of all tracked cells. (C) Circular plot of the angular distribution of trajectories of migrating pAEC from non-asthmatic children represented at discrete 10-degree angular intervals. Importantly, most of the tracked leading edge pAEC migrated consistently forward into the middle of the wound, as indicated by the 100 angle interval marked by a star. (D) Circular plot of the angular distribution of trajectories of migrating pAEC from children with asthma represented at discrete 10-degree angular intervals. Although some leading edge pAEC migrated forward into the wound, asthmatic cells had a varied distribution of trajectories post wounding. Distance (E) was reported as the displacement of a cell from its start point to the endpoint of its migration path. Velocity (F; displacement/time), directionality (G; displacement/total path length), and Forward Migration Index (H; yFMI, y-coordinate of endpoint position relative to the total path length). (E-F) Leading edge pAEC from non-asthmatic children migrated far (E) and fast (F) into the wound site by 10 h post wounding, although, response to wounding was varied. However, leading edge cells of asthmatic children migrated shorter average distances (E) and at slower velocities (F) than their non-asthmatic counterparts ($p<0.001$). (G-H) Notably, leading edge cells of non-asthmatic children migrated directionally (G), and collectively into the center of the wound as shown with high yFMI values (H). Conversely, leading edge pAEC of asthmatic children demonstrated migration trajectories with significantly less directionality (G) and yFMI (H) indicating a loss of coordination in their response to wounding. Cell migration trajectory data were generated from 296 and 228 leading edge cell tracks of non-asthmatic (n=14) and asthmatic (n=9) children respectively. All experiments were completed in two technical replicates. The data was represented as median±IQR, ***$p<0.001$.

Leading edge pAEC of non-asthmatic children responded to the scratch wounding stimulus by migrating directionally towards the center of the wound site (FIG. 2A). The majority of cells migrated consistently forward into the middle of the wound, as indicated by the 10° angle interval (red bar) and 1SD of migration angularity of all tracked cells corresponded to ±17.85° (min-max range: 29.25°-136.57°) (FIG. 2C). However, leading edge pAEC derived from children with asthma showed a dysregulated response to wounding where some cells migrated into the wound site in a random manner and other cells did not migrate very far into the wound and even migrated backwards into the leading edge (FIG. 2C). Unlike their non-asthmatic counterparts, pAEC of asthmatic children did not elicit a coordinated response to wounding. Although some leading edge pAEC migrated forward into the wound, asthmatic cells had a varied distribution of trajectories post wounding where 1SD of migration angularity of tracked cells was 62.54° (min-max range: 2.22°-358.98°) (FIG. 2D).

Furthermore, leading edge pAEC of non-asthmatic children were found to migrate 306.91±121.84 µm into the wound site by 12 h post wounding (FIG. 2E), although the response was varied (min-max range: 88.47-659.10 µm; FIG. 2E). Conversely, asthmatic leading edge cells migrated significantly lower distances 179.27±129.14 µm into the wound site by 12 h post wounding (p<0.001) and displayed a varied response (min-max range: 30.68-824.03 µm; FIG. 2E)

Similarly, leading edge cells from non-asthmatic children migrated at an average velocity of 0.42±0.20 µm/min, although this varied considerably (range: 0.06-1.02 µm/min; FIG. 2F). In contrast, cells from children with asthma migrated significantly slower than their non-asthmatic counterparts with a mean velocity of 0.23±0.20 µm/min (p<0.001) and considerable variability (range: 0.01-1.33 µm/min; FIG. 2F).

Overall, leading edge pAEC of non-asthmatic children migrated efficiently and collectively post wounding into the center of the wound with an average directionality of 0.91±0.08 AU (range: 0.41-1.00 AU) and yFMI of 0.95±0.07 AU (range: 0.49-1.00). No significant relationship was observed between the distance migrated by cells and directionality (Spearman's rho=−0.087; p=0.134) as about 97% of all cell tracks migrated with directionality values greater than 0.70 AU.

Contrastingly, pAEC of children with asthma demonstrated significant loss of directionality and collective migration post wounding towards the center of the wound with an average directionality of 0.61±0.22 AU (range: 0.03-0.96 AU; FIG. 2G) and yFMI of 0.65±0.42 AU (FIG. 21H). Notably, asthmatic cells were found to migrate non-specifically following wound with some leading edge cells migrating backwards into the wounded edge and away from the wound center (yFMI range: −1.00-1.00 AU; FIG. 2H). A weak positive correlation was observed between directionality and distance migrated, where the more directional leading edge cells were the further migrating cells (Spearman's rho 0.332, p<0.001). Furthermore, leading edge pAEC of asthmatic children demonstrated a loss of coordinated response to wounding, with 60% of cells having directionality values less than 0.70 AU, as compared to only 3% of total cells of non-asthmatic children.

Integrins as Regulators of Leading Edge Cell Migration in the Airway Epithelium

Figure 3:
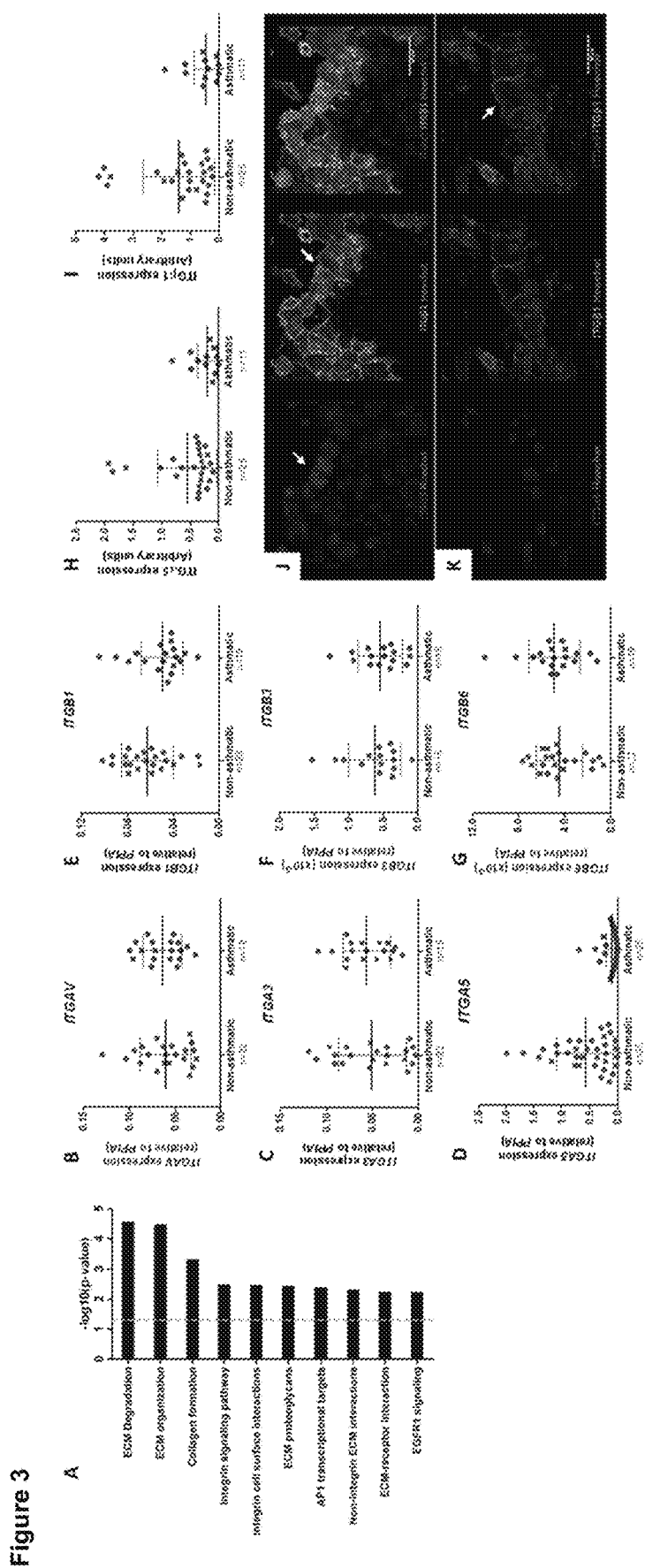
FIG. 3. Differential expression of integrins in pAEC of children with asthma. (A) Canonical pathway analysis of differentially expressed genes between pAEC from the leading edge of the wound at 24 h post wounding from children with asthma compared to corresponding samples of non-asthmatic children. The orange dashed line indicates the statistical significance threshold of 1.3 (Benjamini-Hochberg-adjusted p-value<0.050). Data analysis was performed in InnateDB. (B-G) mRNA expression of integrin α (B-D) and β (E-G) subunits were measured using real time qPCR in ex vivo pAEC of non-asthmatic and asthmatic children. (B-C) mRNA expression of ITGAV and ITGA3 was not significantly different between pAEC from non-asthmatic and asthmatic children. (D) In contrast, mRNA expression of ITGA5 was significantly lower in pAEC from asthmatic children compared to their non-asthmatic counterparts. (E) Furthermore, mRNA expression of ITGB1 was found to be significantly decreased in pAEC from asthmatic children compared to non-asthmatic children. (F-G) No significant differences were observed between pAEC from non-asthmatic and asthmatic children in mRNA expression of ITGB3 and ITGB6. (D-E) ITGA5 and ITGB1 were the most abundantly expressed integrin α and β subunits respectively, in ex vivo pAEC from pediatric cohort. Relative expression of integrin subunits α5 (H) and β1 (I) were measured in pAEC from non-asthmatic and asthmatic children using the On-Cell Western™ assay. (H-I) pAEC cultures from non-asthmatic children expressed integrin α5 (H) and β1 (I) protein on the cell membrane. In contrast, cultured pAEC from asthmatic children displayed significantly lower protein levels of both integrin α5 (H) and β1 (I) on the cell membrane. Protein expression data was normalized to cell number using cell stains DRAQ5™ and Sapphire700. Each dot represents the mean of two replicates from a single patient sample. Data is represented as mean±SD. *Statistical significance relative to non-asthmatic cohort ($p<0.050$; unpaired t-test). (J) Fluorescent immunocytochemical staining of integrin α5 in pAEC from non-asthmatic children demonstrated strong staining on the cell-ECM area and lamellipodia and filopodia extensions of leading-edge cells (arrows). Similarly, integrin β1 was predominantly present in the lamellipodia and filopodia of leading-edge cells, as well as in cell-to-cell junctions (arrows). Although staining for both integrin α5 and β1 was increased on the leading-edge of non-asthmatic cells, integrin β1 showed a specific staining pattern along the leading-edge cells that was almost undetectable in sites distal to the wound. In addition, integrin α5 and β1 showed evidence of co-localization in areas of focal adhesions on the cell basement and cell extensions represented by the orange coloration and arrows. (K) In contrast, pAEC cultures of asthmatic children exhibited weak integrin α5 staining on the cell membrane, following wounding. Integrin α5 staining was not detectable on the lamellipodia and filopodia of migrating cells (arrows). The integrin β1 staining was diffuse in pAEC from asthmatic children. However, integrin β1 staining continued to be localized in cell-to-cell junctions and on the protruding edges of migrating cells (arrows). Leading-edge cells from asthmatic children displayed low formation of lamellipodia and, particularly, filopodia into the wound site (arrows). Both integrin α5 and β1 displayed weak staining intensity along the leading-edge of the wound. The slides were counterstained with Hoechst nuclear stain (blue). Representative images of 5 non-asthmatic and asthmatic pediatric samples. 60× oil immersion objective, NA 1.4, scale bar 50 µm.

Next, the transcriptional profile of leading edge pAEC of children with asthma compared to their non-asthmatic counterparts was investigated to determine major pathways potentially dysregulating their capacity to migrate and repair. Therefore, total RNA was isolated from leading edge pAEC from asthmatic and non-asthmatic cultures at 24 h post wounding and RNA-Sequencing determined a total of 1,153 differentially expressed genes (log 2 fold change: 0.58, adjusted p-value: 0.05). These differentially expressed genes corresponded with at least 50 overrepresented pathways where ECM degradation, organization and collagen formation where in the top three pathways (FIG. 3A). Since exogenous addition of FN, an ECM protein, in pAEC cultures aided repair but did not completely ameliorate the dysregulated asthmatic airway epithelial repair response, the was on the role of the integrin pathway to regulate cell migration and repair in the airway epithelium.

The mRNA expression of FN-binding integrins (i.e. $\alpha V\beta 1$, $\alpha V\beta 3$, $\alpha V\beta 6$, $\alpha 3\beta 1$, $\alpha 5\beta 1$) in the airway epithelium of children was interrogated by qPCR. All of these integrin subunits were found to be transcriptionally expressed by ex vivo pAEC from non-asthmatic children, although at different magnitudes (ITGAV: 0.0704±0.0066 AU; ITGA3: 0.0499±0.0096 AU; ITGA5: 0.5026±0.0959 AU; ITGB1: 0.0652±0.0077 AU; ITGB3: 0.0007±0.0001 AU; ITGB6: 0.0040±0.0007 AU; FIG. 3B-G). Integrin subunit ITGA5 was the most abundantly expressed subunit in pAEC of non-asthmatic children, followed by integrin subunit ITGB1. Importantly, these integrin subunits were the only $\alpha$ and $\beta$ integrin subunits to be significantly decreased in pAEC of children with asthma (ITGA5: 2.5-fold, p=0.003; ITGB1: 1.8-fold, p=0.044; FIG. 3B-G). Expression of the other FN-binding integrin subunits assessed did not significantly differ to their non-asthmatic counterparts (ITGAV, p=0.550; ITGA3, p=0.873; ITGB3, p=0.433; ITGB6, p=0.552; FIG. 3B-G).

The expression of integrin subunits $\alpha 5$ and $\beta 1$ was validated at the protein level using the On-Cell Western™ assay and found that both integrin subunits were expressed in cultured pAEC from non-asthmatic and asthmatic children (FIG. 3H-I). However, integrin subunit $\beta 1$ had relatively higher protein expression levels to integrin subunit $\alpha 5$ in pAEC from non-asthmatic children, 0.63±0.09 AU and 1.78±0.22 AU for $\alpha 5$ and $\beta 1$ integrins respectively (FIG. 3H-I). Similar to the ex vivo expression data, both integrin subunits $\alpha 5$ and $\beta 1$ showed significantly decreased protein expression levels in cultured pAEC from children with asthma where integrin $\alpha 5$ expression was 0.18±0.02 AU (p<0.050) and integrin $\beta 1$ was 0.82±0.12 AU (p<0.050) (FIG. 3H-I).

Having established that integrin $\alpha 5\beta 1$ is the predominant FN-binding integrin in pediatric pAEC and is expressed at significantly lower levels in asthmatic airway epithelium, the expression of integrin $\alpha 5\beta 1$ following in vitro wounding was investigated. Results generated via confocal imaging demonstrated that both integrin subunits $\alpha 5$ and $\beta 1$ (FIG. 3J) displayed higher staining on the leading edge of non-asthmatic cells, as well as cells that had actively migrated into the wound site. Integrin α5 showed a diffuse staining pattern and was predominantly present on the cell-ECM area localizing on the lamellipodia and filopodia of leading edge cells (arrows, FIG. 3J). Integrin α5 showed higher staining intensity along the first row of leading edge cells, whilst cells in distal sites to the wound continued to stain positively for integrin α5, although at lower staining intensity (FIG. 3J). Similarly, integrin β1 was predominantly present in the lamellipodia and filopodia of leading edge cells, as well as in cell-to-cell junctions (arrows, FIG. 3J). Notably, integrin β1 showed a specific staining pattern along the leading edge cells that was almost undetectable in sites distal to the wound, about 2 to 3 cell layers behind the wound site (FIG. 3J). In addition, integrin α5 and β1 showed evidence of co-localization in areas of focal adhesions on the cell basement and cell extensions represented by the orange coloration and arrows (FIG. 3J).

Following wounding, integrin α5 and β1 (FIG. 3K) staining on the cell membrane of pAEC from asthmatic children was lower than that of their non-asthmatic counterparts (FIG. 3J). Integrin α5 was still predominantly present in the cell-ECM basement surface, however it was not detectable on the lamellipodia and filopodia of migrating cells (arrows, FIG. 3K). Furthermore, integrin α5 did not show the same specific upregulation of staining in the leading edge cells from asthmatic children (FIG. 3K) seen in the non-asthmatic counterparts (FIG. 3J). The integrin β1 staining was more diffuse in pAEC from asthmatic children (FIG. 3K) compared to that observed in pAEC from non-asthmatic children. Integrin β1 staining continued to be localized in cell-to-cell junctions and on the protruding edges of migrating cells (arrows, FIG. 3K). Conversely, leading edge cells from asthmatic children displayed reduced formation of lamellipodia and, particularly, filopodia into the wound site (arrows, FIG. 3K), compared to non-asthmatic controls (FIG. 3J). Although integrin β1 showed evidence of increased staining intensity along the leading edge cells (FIG. 3K), the staining pattern was less intense than in pAEC from non-asthmatic children. Finally, integrin α5 and β1 showed minimal evidence of co-localization on the cell basement and cell extensions, indicating a potential loss of integrin α5β1 hetero-dimerization on the cell membrane (FIG. 3K).

Figure 4:
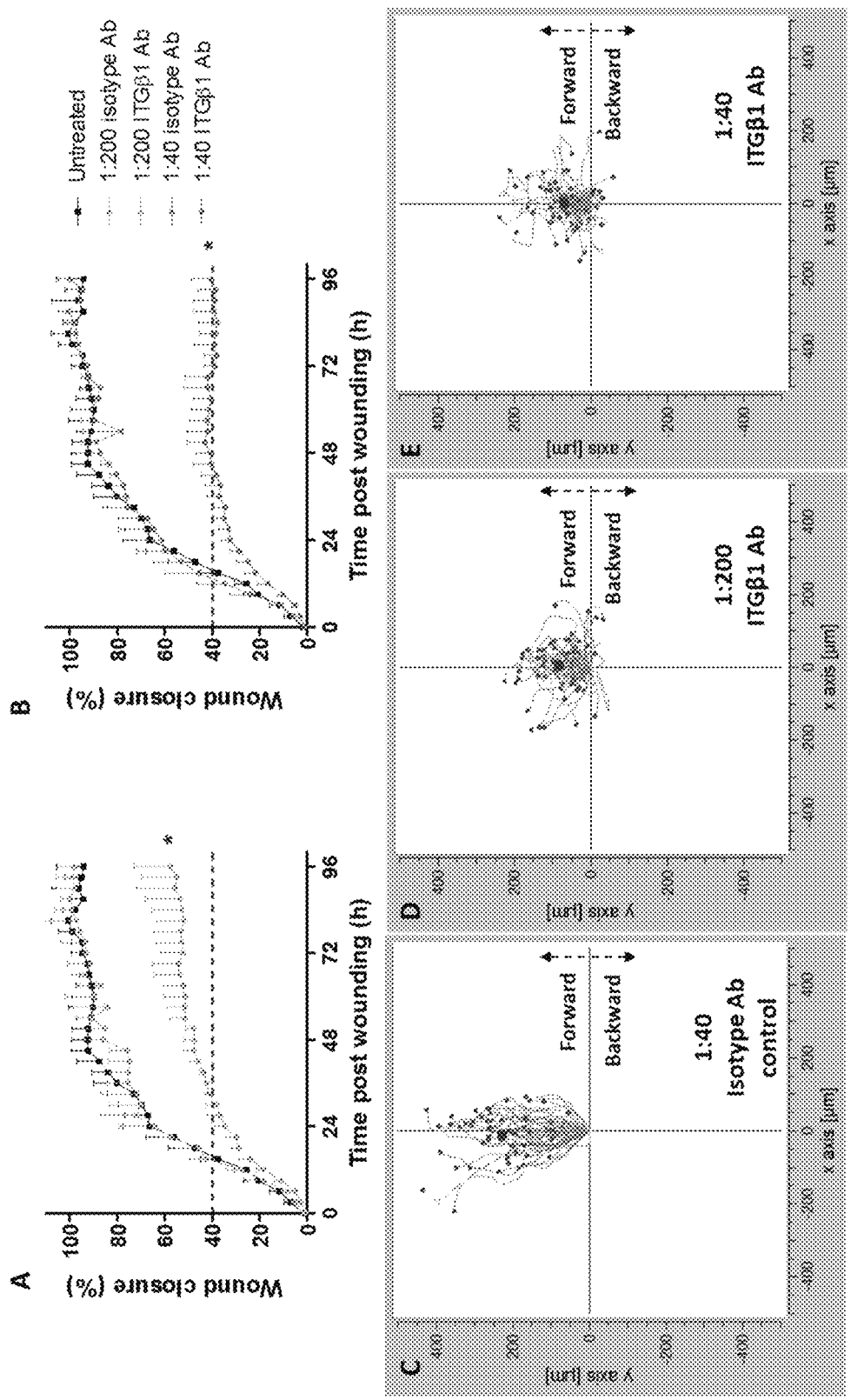
FIG. 4. Inhibition of β1 integrin contributes to defective cell migration and repair in asthmatic airway epithelium. (A-B) Wound closure rates of pAEC cultures from non-asthmatic children treated with 1:200 (A) and 1:40 (B) dilutions of functional blocking antibody against β1 integrins (IgG1κ, P5D2), matching isotype control antibody (IgG1κ, MOPC-21) dilutions, or untreated were determined. Blocking β1 integrin function significantly reduced pAEC wound closure rates ($p<0.050$) (n=4 children; mean±SD) in a dose-dependent manner. Matching dilutions of isotype control antibody or untreated pAEC cultures reached full wound closure by 48 h to 72 h post wounding (n=4 children; mean±SD). (C-E) Migration trajectories of leading edge pAEC migrating towards the wound site (n=60 tracks from cultures of 4 non-asthmatic children). (C) Cultures treated with isotype antibody (Ab) (1:40 dilution) displayed comparable migration patterns to untreated pAEC from non-asthmatic children. However, cultures treated with 1:200 (D) and 1:40 (E) dilutions of anti-β1 integrin antibody in culture media migrated less far into the wound, lacking cell directionality and specificity towards the wound center. Individual cell tracks were transposed so that each track had its start at the origin.

To confirm the functional role of reduced integrin levels during airway epithelial repair, functional blocking experiments were performed in pAEC from non-asthmatic children. Two doses of anti-β1 integrin antibody (Ab) were used, a low dilution (1:40) and high dilution (1:200). This approach was undertaken to simulate strong reduction and mild reduction of expression levels of β1 integrin respectively, reflecting conditions previously observed in asthmatic airway epithelium (refer to FIGS. 4A and B). As shown in FIGS. 4A and B, blocking of integrin β1 resulted in the inhibition of wound closure of pAEC from non-asthmatic children in a dose-dependent manner reflecting equivalent levels of wound closure to pAEC from asthmatic children. Specifically, 1:200 anti-integrin β1 antibody dilution lead to 57.51±15.61% wound closure (FIG. 4A) and 1:40 antibody dilution resulted in 40.29±8.40% wound closure by 96 h post wounding (FIG. 4B). Equivalent dilutions of the IgG1K isotype control antibody and untreated control resulted in wound closure rates of 98.03±7.10% (1:200 isotype control), 99.95±4.73% (1:40 isotype control) and 94.09±11.38% (untreated control), at 96 h post wounding, respectively (FIGS. 4A and B).

Figure 5:
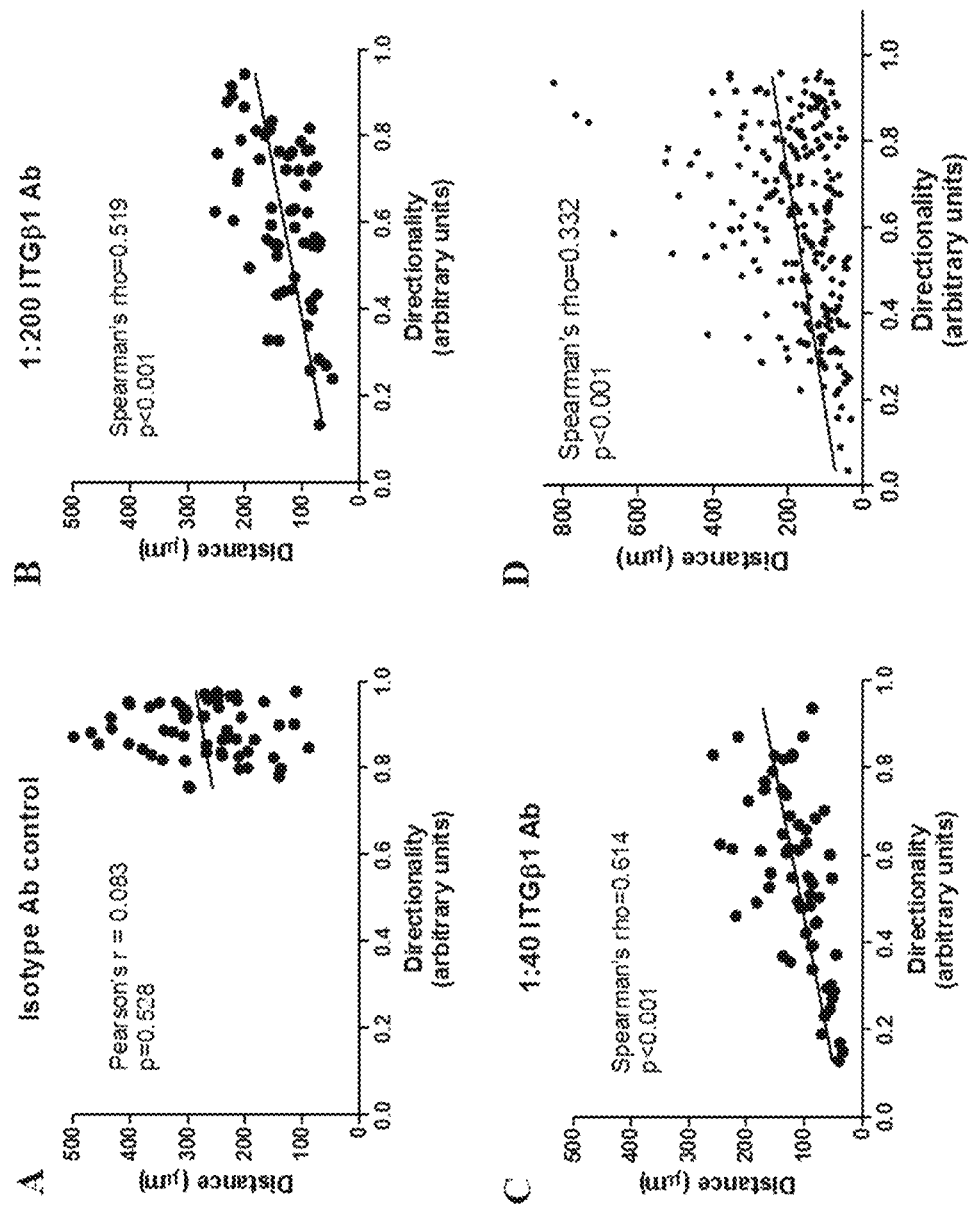
FIG. 5. Relationship between cell directionality and distance migrated. (A) Isotype antibody (1:40 dilution) treated pAEC cultures from non-asthmatic children did not show a significant correlation between cell directionality and distance as most leading edge cells migrated highly directionally. (B-C) However, pAEC cultures from non-asthmatic children treated with 1:200 (B) and 1:40 (C) dilutions of anti-β1 integrin antibody demonstrated a positive relationship between directionality and distance migrated, where cells migrating further into the wound also migrated more directionally. (D) Importantly, pAEC cultures from asthmatic cultures demonstrated a similar positive relationship between directionality and distance migrated suggesting that loss of integrin β1 reduced the capacity of pAEC to migrate directionally and far into the wound. Individual cell tracks were transposed so that each track had its start at the origin.

Since decreased expression of integrin α5β1 in pAEC of asthmatic children was associated with dysregulated leading edge pAEC migration pattern the leading edge migration analysis was extended to the integrin β1 inhibition studies. Primary cultures treated with isotype antibody displayed a physiological response to wounding (FIG. 4C), however dysregulated cell migration was observed following integrin β1 inhibition (FIGS. 4D and I). Cell cultures from non-asthmatic children treated with either 1:200 (FIG. 4D) or 1:40 (FIG. 4E) dilution of integrin β1 blocking antibody migrated in a similar pattern to pAEC of asthmatic children post wounding. Specifically, leading edge pAEC did not migrate as far into the wound, lost their directionality and finally their specificity towards the wound center with some cells moving backwards into the wound edge. Furthermore, there was a significant reduction in the following migration parameters; mean distance (1:40 isotype Ab control: 274.60±92.70 μm, 1:200 ITGb1 Ab: 134.30±53.27 μm, 1:40 ITGb1 Ab: 113.50±53.45 μm, p<0.001; Table 3), cell velocity (1:40 isotype Ab control: 0.33±0.12 μm/min, 1:200 ITGb1 Ab: 0.16±0.08 μm/min, 1:40 ITGb1 Ab: 0.14±0.07 μm/min, p<0.001; Table 2), directionality (1:40 isotype Ab control: 0.89±0.06 AU, 1:200 ITGb1 Ab: 0.62±0.19 AU, 1:40 ITGb1 Ab: 0.55±0.20 AU, p<0.001; Table 2) and yFMI (1:40 isotype Ab control: 0.96±0.06 AU, 1:200 ITGb1 Ab: 0.72±0.34 AU, 1:40 ITGb1 Ab: 0.64±0.51 AU, p<0.001; Table 3). Similarly to pAEC of non-asthmatic children (FIG. 5C), the isotype antibody treated cells did not display a significant correlation between cell directionality and mean distance (Pearson's r 0.083, p=0.528; FIG. 5A). However, the positive correlation between cell directionality and mean distance previously reported in pAEC of children with asthma (FIG. 5D) was reproduced in the 1:200 (FIG. 5B) and 1:40 (FIG. 5C) anti-integrin β1 treated cells with Spearman's rho values of 0.519 and 0.614 and p<0.001 for both treatment groups, respectively.

TABLE 3

Migration parameters of pAEC tracks.

| Migration Parameters | Antibody dilution | Mean | SD | p-value |
|---|---|---|---|---|
| Displacement (μm) | 1:40 isotype | 235.22 | 92.70 | n/a |
| | 1:200 P5D2 | 114.63 | 53.27 | P < 0.001 |
| | 1:40 P5D2 | 97.19 | 53.45 | P < 0.001 |
| Velocity (μm/min) | 1:40 isotype | 0.33 | 0.12 | n/a |
| | 1:200 P5D2 | 0.16 | 0.08 | P < 0.001 |
| | 1:40 P5D2 | 0.14 | 0.07 | P < 0.001 |
| Directionality (A.U.) | 1:40 isotype | 0.89 | 0.06 | n/a |
| | 1:200 P5D2 | 0.62 | 0.19 | P < 0.001 |
| | 1:40 P5D2 | 0.55 | 0.20 | P < 0.001 |
| yFMI (A.U.) | 1:40 isotype | 0.96 | 0.06 | n/a |
| | 1:200 P5D2 | 0.72 | 0.34 | P < 0.001 |
| | 1:40 P5D2 | 0.64 | 0.51 | P < 0.001 |

SD, standard deviation;
A.U., arbitrary units;
yFMI, y-axis forward migration index;
n/a, not applicable.

Akt Signaling is Required for Integrin α5β1 Expression and Efficient Airway Epithelial Cell Migration and Repair Following Injury To directly examine the transcriptional regulators of integrin α5β1 expression in primary airway epithelial cells of children with asthma, global transcriptional expression patterns from the leading edge cells from cultures of children with and without asthma at 24 h post wounding, were investigated by employing prior knowledge built into the upstream regulator analysis package within Ingenuity® Systems (IPA®, QIAGEN, Redwood City, Calif., USA, www.qiagen.com/ingenuity). A number of upstream transcriptional regulators of integrin subunit ITGA5 and/or ITGB1 expression were identified, as depicted in Table 4. Briefly, 35 upstream regulators predicted to be activated (2 regulators) or inhibited (33 regulators) were identified that have been previously shown to regulate gene expression of either integrin subunit individually or both subunits concurrently. Analysis revealed several growth factors of interest including; EGF, ErbB2, TGFβ, and PDGF, as well as signaling molecules and transcription factors such as PI3K/AKT1, mitogen-activated kinases (MEK, MAPK) and NFκB. Unbiased network analysis of these upstream regulators identified some of these candidates as highly interconnected genes, or hubs, including AKT1, ERBB2 and ITGB1.

Pathway analysis of published transcriptomic datasets using either ex vivo airway samples (McErlean, Berdnikovs et al., Genome Med. 2014; 6(1): 1., Heymann, Nguyen et al., PLoS One. 2017 May 26; 12(5):e0178096) or cultured airway epithelial cells (Bochkov, Hanson et al. 2010 Mucosal Immunol. 2010; 3(1): 69-80) from adult patients with asthma also identified PI3K/Akt signaling as a common pathway implicated in asthma (data not shown). Importantly, PI3K/Akt signaling was found to be enriched both at baseline conditions in patients with asthma, and following viral-induced exacerbations that was uniquely associated with defective resolution of wound repair (McErlean, Berdnikovs et al., Genome Med. 2014; 6(1): 1).

TABLE 4

Upstream transcriptional regulators of integrin α5β1.

| Upstream regulator | Activation z-score | −log10(p-value) |
|---|---|---|
| ITGA5 only | | |
| CTNNA1 | −2.9 | 12.3 |
| PDGF (complex) | −2.0 | 3.2 |
| SPDEF | −2.0 | 3.9 |
| BMP6 | −2.0 | 6.0 |
| ITGB1 | −2.0 | 4.9 |
| APOE | 2.0 | 3.2 |
| ITGB1 only | | |
| RAF1 | −3.4 | 18.2 |
| HGF | −3.3 | 17.5 |
| MAPK3 | −3.0 | 2.7 |
| MYCN | −2.9 | 2.7 |
| IL2 | −2.8 | 12.7 |
| F2 | −2.7 | 9.3 |
| EGF | −2.6 | 13.7 |
| PITX2 | −2.6 | 2.0 |
| IL15 | −2.4 | 5.3 |
| PKM | −2.4 | 3.3 |
| VEGF | −2.4 | 15.6 |
| MEK | −2.2 | 7.7 |
| ANGPT1 | −2.2 | 2.3 |
| TP63 | −2.2 | 21.4 |
| IRF4 | −2.2 | 2.0 |
| NFKBIA | 2.0 | 12.1 |
| ITGA5 and ITGB1 | | |
| PDGF BB | −3.3 | 13.9 |
| HRAS | −3.1 | 18.0 |
| PI3K (complex) | −2.8 | 5.1 |
| ERBB2 | −2.3 | 23.5 |
| MAP2K1 | −2.2 | 7.2 |
| AKT1 | −2.2 | 2.6 |
| EDN3 | −2.2 | 2.8 |
| FGF2 | −2.0 | 10.2 |

TABLE 4-continued

Upstream transcriptional regulators of integrin α5β1.

| Upstream regulator | Activation z-score | −log10(p-value) |
|---|---|---|
| CSF1 | −2.0 | 5.6 |
| TGFB1 | −2.0 | 42.0 |
| EDN1 | −2.0 | 6.2 |
| SMARCA4 | −2.0 | 13.2 |
| CYR61 | −2.0 | 2.5 |

Figure 6:
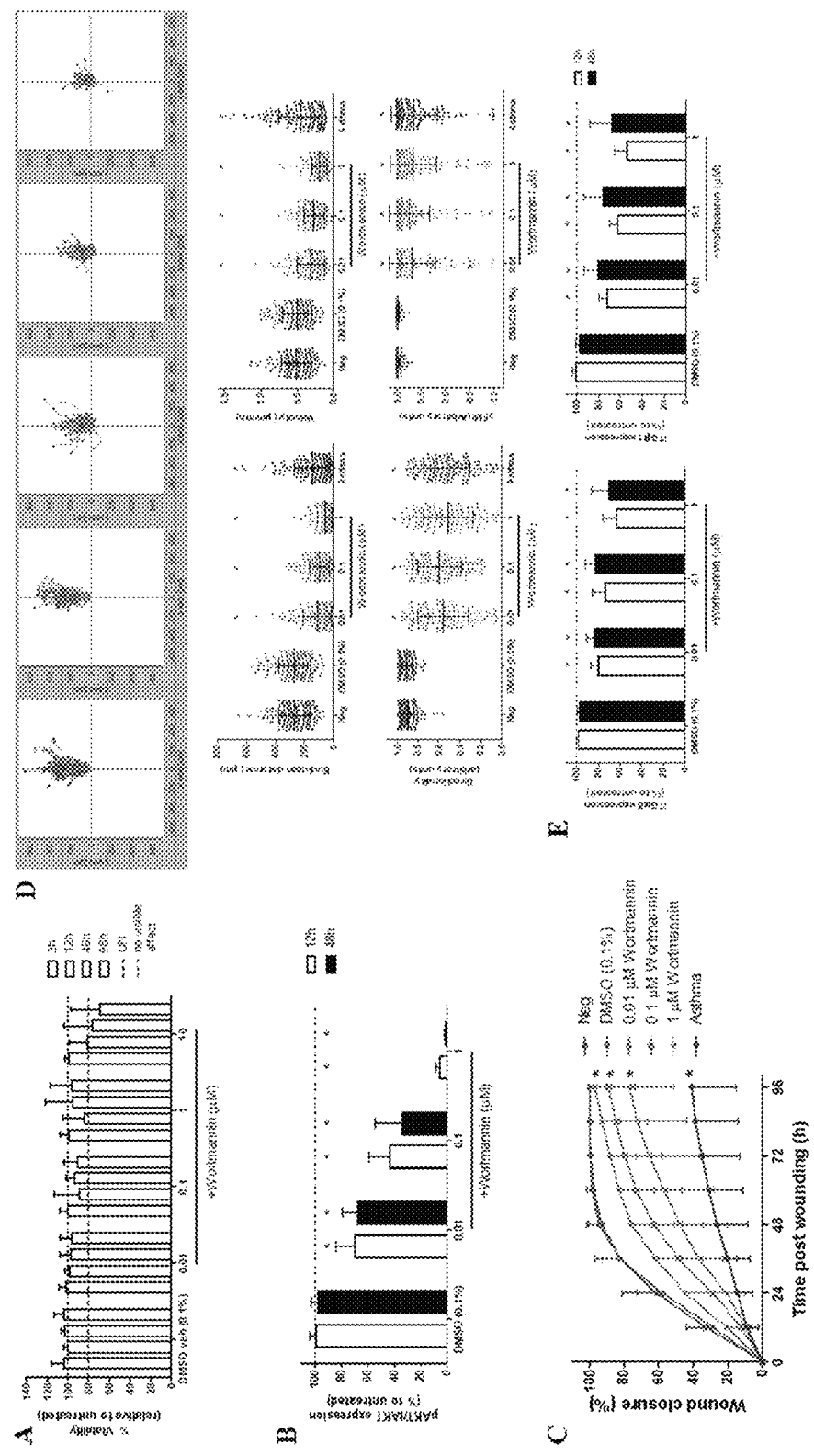
FIG. 6. Dampened PI3K/Akt signaling inhibits airway epithelial repair via downregulation of integrin α5β1 expression. (A-E) Monolayer pAEC cultures from non-asthmatic children were treated with different concentrations (0.01, 0.1, 1, 10 µM) of the pan-PI3K inhibitor, Wortmannin. (A) Cell viability was determined using the MTS assay and all concentrations bar 10 µM did not cause significant cytotoxicity. (B) Wortmannin inhibited activation of PI3K and phosphorylation of its downstream effector, Akt (serine residue 473), at 12 h and 48 h post treatment, as determined by In-Cell™ Western assay. (C) Treatment of pAEC cultures from non-asthmatic children with Wortmannin at the time of scratch wounding resulted in a concentration-dependent reduction in wound closure rates, although DMSO vehicle control was not significantly altered compared to untreated cultures. (D) Tracking of individual leading edge pAEC identified that PI3K inhibition inhibited distance migrated, velocity, directionality and centrality (yFMI) of Wortmannin-treated cultures in a concentration-dependent manner. (E) Inhibition of PI3Ks in pAEC cultures from non-asthmatic children resulted in significant reduction of integrin α5 and β1 cell membrane expression in a concentration-dependent manner at 12 h and 48 h post Wortmannin treatment. All experiments were completed with pAEC cultures from 6 non-asthmatic children and data was represented as mean±SD.

This study explored whether dysregulated signaling via the PI3K/Akt pathway exists in the epithelia of children with asthma, thereby reducing expression of integrin α5β1 and impairing the capacity of pAEC to migrate and repair efficiently following injury. Protein expression analysis of the Akt pathway determined that although there was abundant total Akt expression, a significant reduction of Akt phosphorylation at serine 473 existed in pAEC of children with asthma compared to non-asthmatic controls (FIG. 6A). To determine the effect of reduced signaling via the PI3K/Akt pathway on wound repair, pAEC cultures from non-asthmatic children were treated with Wortmannin, a broad spectrum inhibitor of all PI3Ks. Wortmannin treatment did not have a significant cytotoxic effect at the lower doses (0.01-1 μM), however a significant loss of viability was observed with 10 μM Wortmannin ($p<0.050$; FIG. 6B). Furthermore, the activated levels of Akt were significantly reduced following as little as 1 h to at least 24 h treatment with Wortmannin (FIG. 6C). Significantly, inhibition of PI3K signaling in non-asthmatic cultures resulted in a dose-dependent attenuation of wound closure rates (FIG. 6D) and migration of leading edge cells (FIG. 6E). Finally, inhibition of PI3K signaling resulted in significant reduction of integrin α5β1 protein expression suggesting that loss of PI3K signaling in asthma could directly impact on integrin expression and epithelial cell migration and repair.

Figure 7:
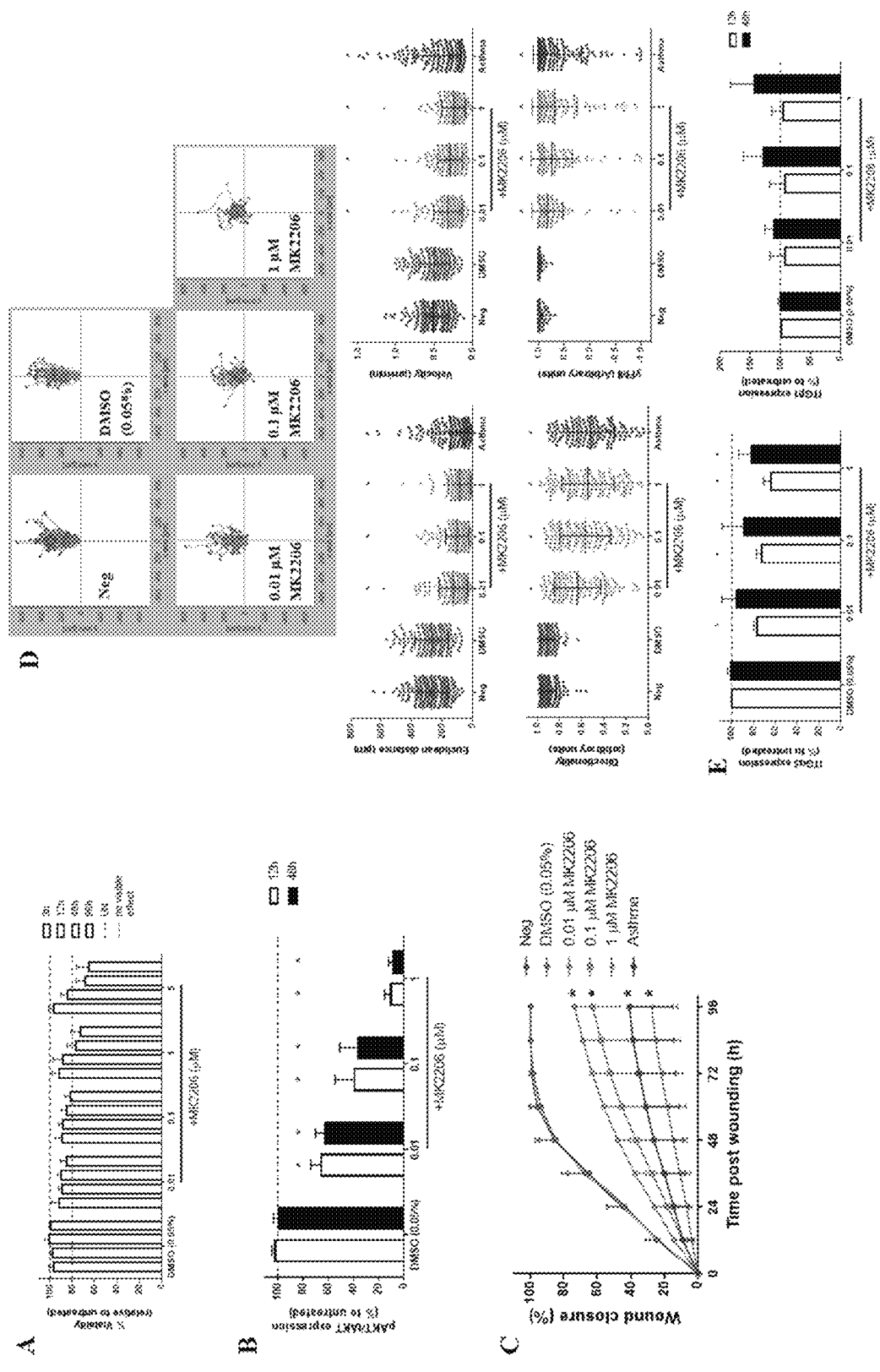
FIG. 7. Specific inhibition of Akt signaling abrogates airway epithelial repair via downregulation of integrin α5, but not β1 expression. (A-E) Monolayer pAEC cultures from non-asthmatic children were treated with different concentrations (0.01, 0.1, 1, 5 μM) of the specific Akt inhibitor, MK2206. (A) Cell viability was determined using the MTS assay and all concentrations bar 5 μM did not cause significant cytotoxicity. (B) MK2206 inhibited activation of Akt (serine residue 473), at 12 h and 48 h post treatment, as determined by In-Cell™ Western assay. (C) Treatment of pAEC cultures from non-asthmatic children with MK2206 at the time of scratch wounding resulted in a concentration-dependent reduction in wound closure rates, although DMSO vehicle control was not significantly altered compared to untreated cultures. (D) Tracking of individual leading edge pAEC identified that Akt inhibition inhibited distance migrated, velocity, directionality and centrality (yFMI) of MK2206-treated cultures in a concentration-dependent manner. (E) Inhibition of Akt in pAEC cultures from non-asthmatic children resulted in significant reduction of integrin α5, but not integrin β1 cell membrane expression in a concentration-dependent manner at 12 h post Wortmannin treatment. Significant reduction of integrin α5 cell membrane expression was also detected at 48 h with 1 μM MK2206 treatment, but not with the lower concentrations of MK2206. All experiments were completed with pAEC cultures from 6 non-asthmatic children and data was represented as mean±SD.

As Wortmannin has inhibitory activity on class 1, 11 and III PI3K members, as well as other signaling pathways like PI4Ks, MLCK and PLK1 at micromolar concentrations, a specific inhibitor against Akt, MK2206, was utilized to confirm the findings of this study (FIG. 7). Of note, treatment of pAEC cultures of non-asthmatic children with increasing concentrations of MK2206 (0.01-5 μM) resulted in significant inhibition of Akt activation, wound closure and leading edge cell migration, particularly distance migrated, velocity, directionality and forward migration index compared to matched vehicle treated non-asthmatic cultures, recapitulating the asthmatic phenotype (FIG. 7D). Specific inhibition of Akt with MK2206 resulted in a concentration-dependent inhibition of integrin α5 cell membrane protein expression following 12 hours treatment, however significant inhibition of integrin α5 expression was only observed with 1 μM MK2006 with 48 hours treatment (FIG. 7E). Conversely, Akt inhibition did not have a significant effect on integrin β1 cell membrane protein expression at 12 hours treatment. These data suggest that a combination of Akt and non-Akt-dependent PI3K signaling may be involved in the dampened integrin α5β1 expression (FIG. 7E).

Figure 8:
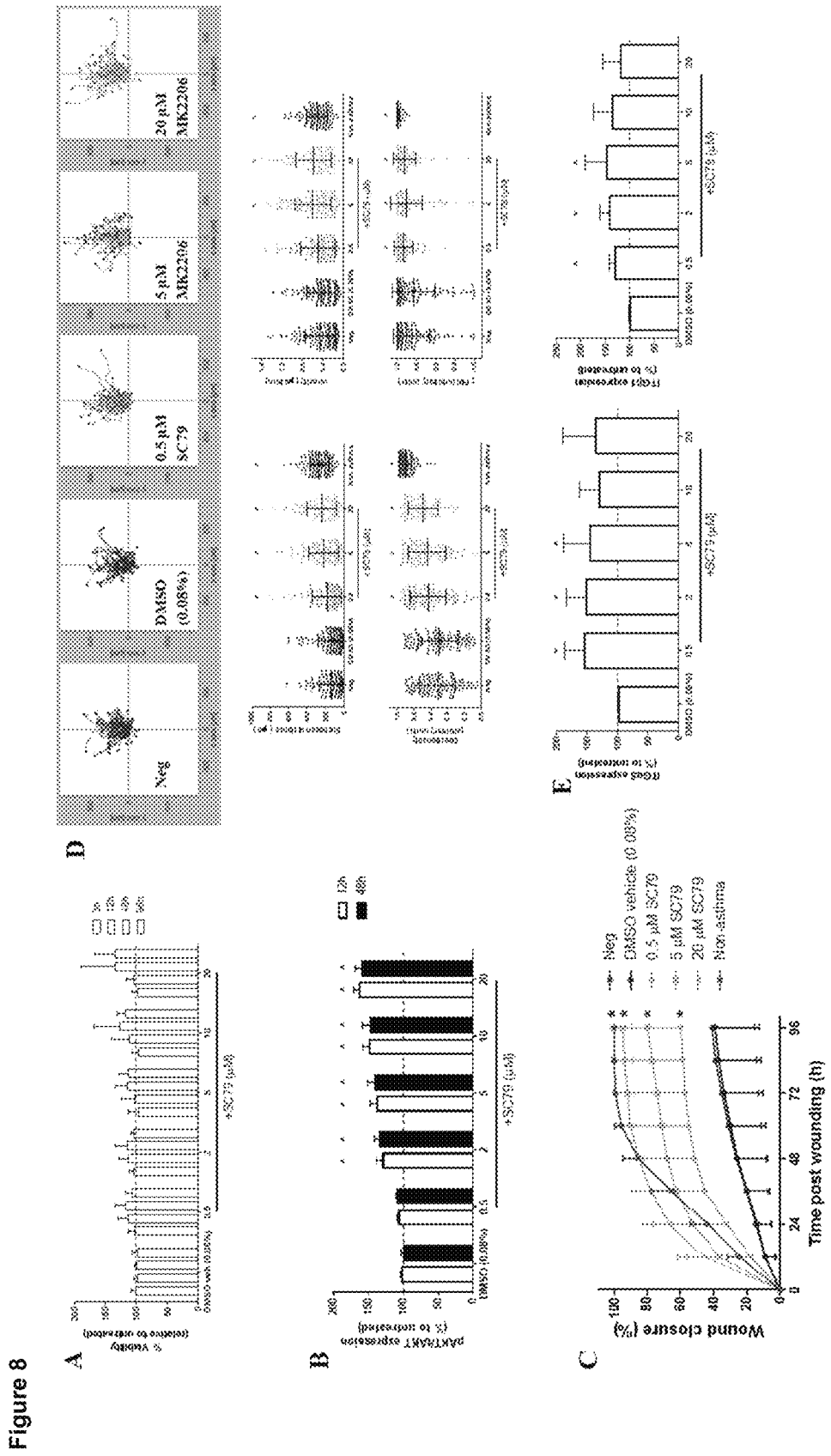
FIG. 8. Activation of Akt signaling enhances asthmatic airway epithelial repair and upregulation of integrin α51 expression. (A-E) Monolayer pAEC cultures from asthmatic children were treated with different concentrations (0.5, 2, 5, 10, 20 μM) of the specific Akt activator, SC79. (A) Cell viability was determined using the MTS assay and all concentrations did not cause significant cytotoxicity. (B) SC79 treatment resulted in phosphorylation of Akt (serine residue 473), at 12 h and 48 h post treatment, as determined by In-Cell™ Western assay. (C) Treatment of pAEC cultures from asthmatic children with SC79 at the time of scratch wounding resulted in a concentration-dependent increase in wound closure rates, although DMSO vehicle control was not significantly altered compared to untreated cultures. (D) Tracking of individual leading edge pAEC identified that Akt activation stimulated distance migrated, velocity, directionality and centrality (yFMI) of SC79-treated asthmatic cultures in a concentration-dependent manner. (E) Significant activation of integrin α5 and β1 cell membrane expression was observed in asthmatic cultures treated with 0.5, 2 and 5 μM SC79 at 12 h and 48 h. All experiments were completed with pAEC cultures from 6 non-asthmatic children and data was represented as mean±SD.

SC79 Targets the Akt/α5β1 Integrin Pathway to Enhance Airway Epithelial Cell Migration and Repair in Asthma To test the direct effect of Akt phosphorylation on epithelial cell migration and repair via the Akt-α5β1 integrin axis, pAEC cultures of children with asthma were treated with increasing concentrations (0.1-20 μM) of the Akt activator, SC79 over different times (3-96 h). SC79 is 2-Amino-6-chloro-α-cyano-3-(ethoxycarbonyl)-4H-1-benzopyran-4-acetic acid ethyl ester. SC79 treatment did not alter cell viability of pAEC cultures (FIG. 8A); however, it did augment Akt signaling in a concentration-dependent manner (FIG. 8B). Importantly, SC79 treatment significantly enhanced wound closure of pAEC of children with asthma in a concentration-dependent manner compared to vehicle and untreated controls (FIG. 8C). Similarly, SC79 stimulated leading edge cell migration where treated asthmatic cells migrated higher distance, velocity, directionality and towards the center of the wound (yFMI; FIG. 8D). Importantly, stimulation of Akt signaling in pAEC of children with asthma restored their integrin α5 and β1 expression to equivalent levels to those of non-asthmatic children (FIG. 8E). These data suggest that stimulation of the PI3K-Akt signaling pathway upregulates of integrin α5β1 expression and rescues their defective migration and repair phenotype.

Celecoxib Targets the PI3K/Akt/Integrin α5β1 Pathway to Enhance Asthmatic Airway Epithelial Repair Celecoxib (Celebrex), an FDA-approved selective COX2 inhibitor used in the treatment of rheumatoid arthritis, juvenile arthritis and pain management, has been reported to activate PI3K/Akt and mitochondrial redox signaling to enhance HO-1-mediated anti-inflammatory activity in vascular endothelium and lung macrophages from patients with cystic fibrosis. Thus, the hypothesis that celecoxib could enhance asthmatic airway epithelial repair through the activation of PI3K/Akt signaling and integrin α5β1 expression was tested. Furthermore, the dimethyl-celecoxib analogue that lacks inhibitory activity against COX2 enzymes, was also interrogated to determine if any beneficial effects on epithelial repair were independent of COX2 inhibition. Primary airway epithelial cells from children with asthma were treated with celecoxib or dimethyl-celecoxib at various concentrations (0.01-10 μM) to determine any deleterious effects these compounds have on epithelial cells. Interestingly, these drugs were not cytotoxic at these concentrations (FIGS. 9A and 10A).

Figure 9:
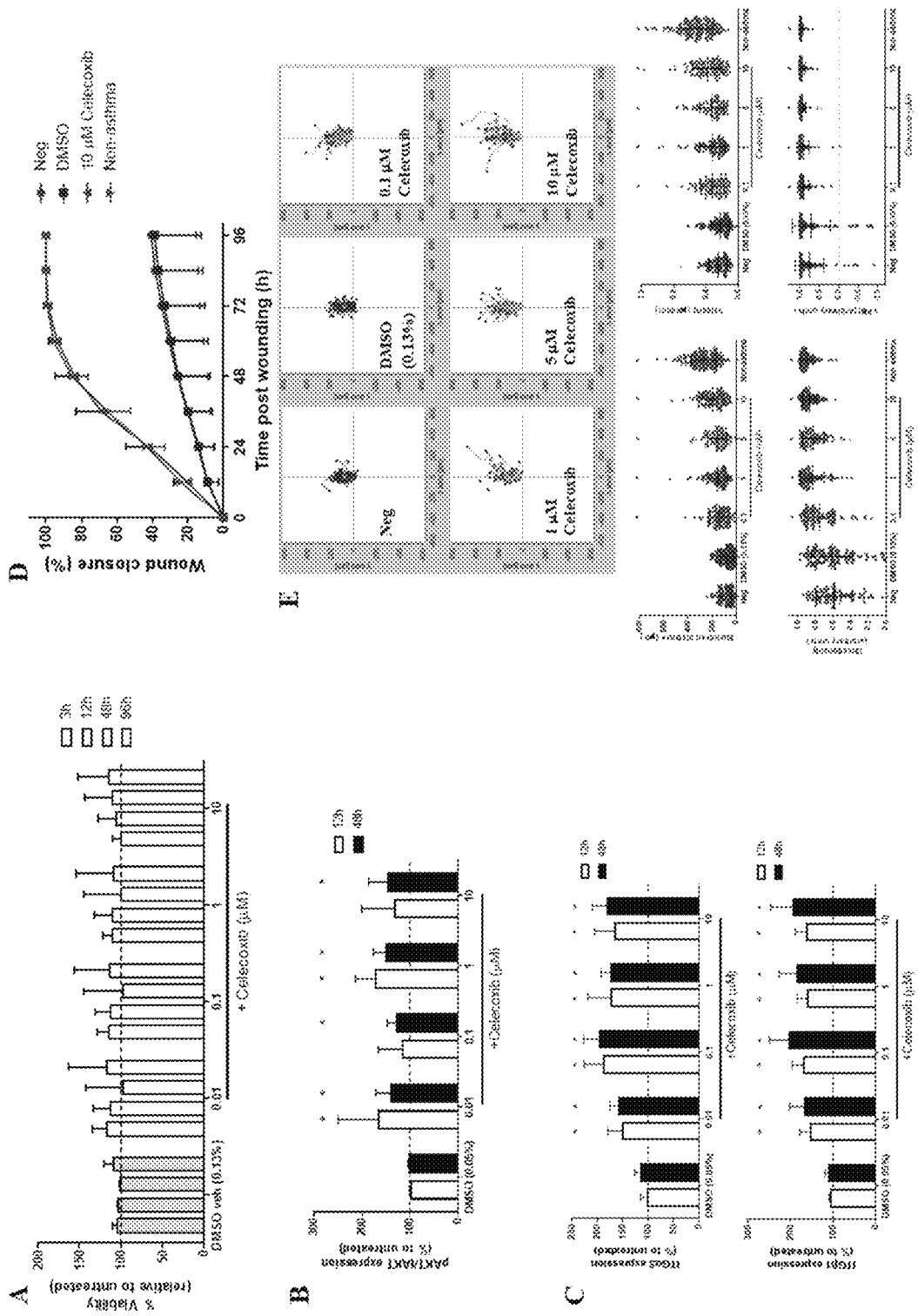
FIG. 9. Asthmatic airway epithelial repair can be modulated by COX2 inhibitor, Celecoxib, treatment via the PI3K/Akt/integrin α5β1 pathway axis. (A-E) Monolayer pAEC cultures from asthmatic children were treated with different concentrations (0.01, 0.1, 1, 10 μM) of COX2 inhibitor, Celecoxib. (A) Cell viability was determined using the MTS assay and all concentrations did not cause significant cytotoxicity. (B) Celecoxib treatment resulted in phosphorylation of Akt (serine residue 473), at 12 h and 48 h post treatment, as determined by In-Cell™ Western assay. (C) Significant activation of integrin α5 and β1 cell membrane expression was observed in treated asthmatic cultures in a concentration-dependent manner at both 12 h and 48 h. (D) Treatment of pAEC cultures from asthmatic children with Celecoxib at the time of scratch wounding resulted in increase in wound closure rates where complete repair was observed with 10 μM Celecoxib treatment. (E) Tracking of individual leading edge pAEC identified that Celecoxib treatment stimulated distance migrated, velocity, directionality and centrality (yFMI) of treated asthmatic cultures in a concentration-dependent manner. All experiments were completed with pAEC cultures from 6 non-asthmatic children and data was represented as mean±SD.
Figure 10:
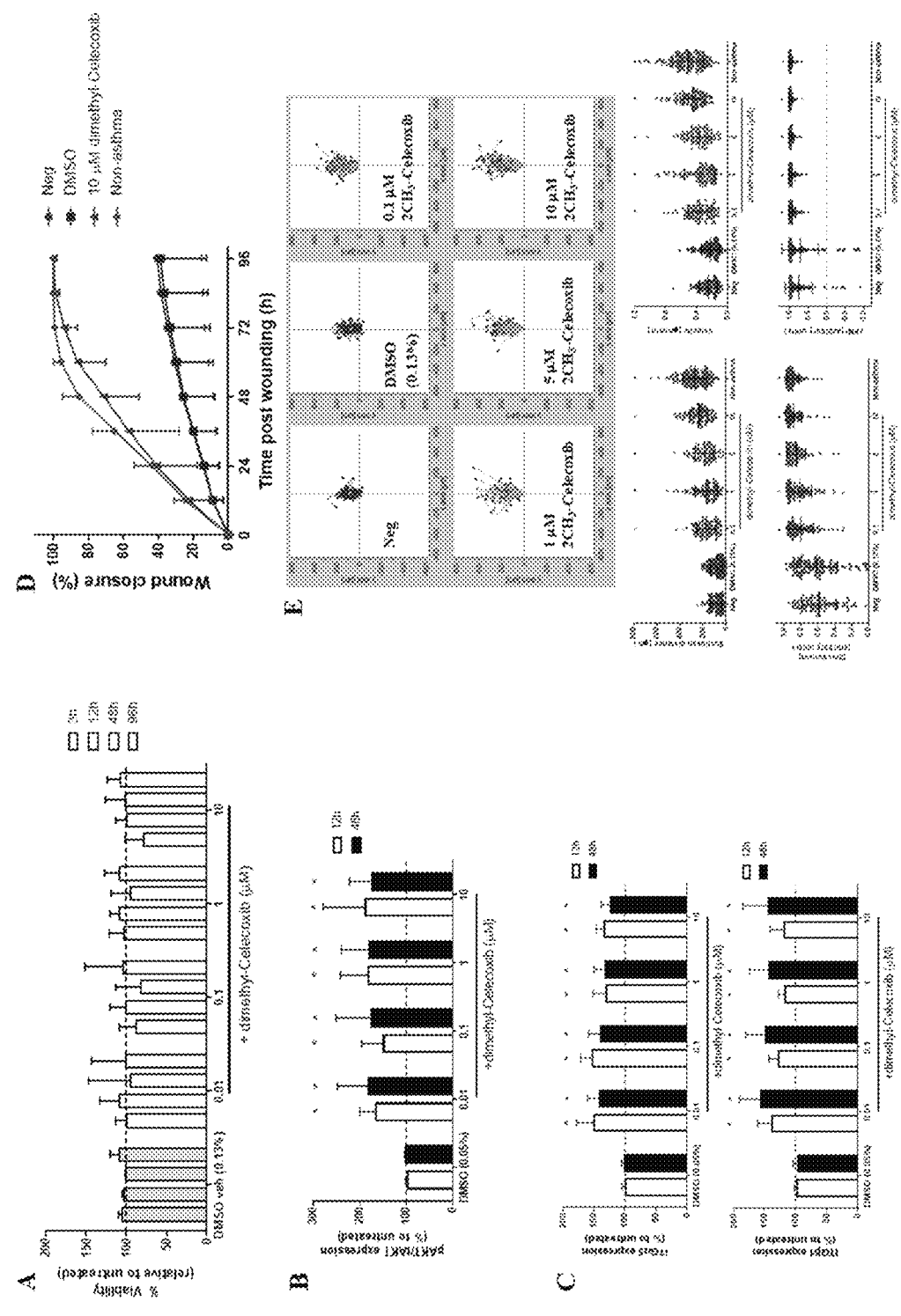
FIG. 10. Asthmatic airway epithelial repair can be modulated by dimethyl-Celecoxib, in a COX2-independent manner, via the PI3K/Akt/integrin α5β1 pathway axis. (A-E) Monolayer pAEC cultures from asthmatic children were treated with different concentrations (0.01, 0.1, 1, 10 μM) of dimethyl-Celecoxib, a Celecoxib analogue lacking COX2 inhibitory activity. (A) Cell viability was determined using the MTS assay and all concentrations did not cause significant cytotoxicity. (B) Dimethyl-Celecoxib treatment resulted in phosphorylation of Akt (serine residue 473), at 12 h and 48 h post treatment, as determined by In-Cell™ Western assay. (C) Significant activation of integrin α5 and β1 cell membrane expression was observed in treated asthmatic cultures in a concentration-dependent manner at both 12 h and 48 h. (D) Treatment of pAEC cultures from asthmatic children with dimethyl-Celecoxib at the time of scratch wounding resulted in increase in wound closure rates where complete repair was observed with 10 μM dimethyl-Celecoxib treatment. (E) Tracking of individual leading edge pAEC identified that dimethyl-Celecoxib treatment stimulated distance migrated, velocity, directionality and centrality (yFMI) of treated asthmatic cultures in a concentration-dependent manner. All experiments were completed with pAEC cultures from 6 non-asthmatic children and data was represented as mean±SD.

Celecoxib and dimethyl-celecoxib treatment activated PI3K/Akt signaling (FIGS. 9B and 10B) and upregulate cell membrane expression of integrin α5β1 protein in asthmatic cultures (FIGS. 9C and 10C). Importantly, treatment of asthmatic cultures with either celecoxib or dimethyl-celecoxib resulted in significant enhancement of airway epithelial repair in a concentration-dependent manner, where 10 μM treatment stimulated full wound closure in asthmatic cultures (FIGS. 9D and 10D). Finally, celecoxib and dimethyl-celecoxib stimulated repair by enhancing leading edge cell migration immediately following wounding (FIGS. 9E and 10E). In fact, treated cultures migrated longer distances, at higher velocity, directionality and towards the wound center compared to vehicle treated or untreated asthmatic cultures (FIGS. 9E and 10E).

Example 6: Activity of Celecoxib and Celecoxib Analogues

Patient Demographics and Sample Collection

Two cohorts were used in this study: 2 children with mild asthma (2.6-3.2 years, 2 males), who did not previously receive any corticosteroid therapy, and 2 children with no history of asthma (2.9-3.0 years, 1 male). Subjects were undergoing elective surgery for non-respiratory related conditions and had no pre-existing bacterial or viral chest infection at the time of recruitment. Asthma was defined as physician-diagnosed based upon physician documented wheezing episodes in the 12 months preceding their recruitment and confirmed by positive responses on the International Study of Asthma and Allergies in Children (ISAAC) and American Thoracic Society (ATS) respiratory questionnaires All children had mild asthma, such that none are receiving glucocorticosteroids (inhaled or oral) and less than 10% are taking beta-agonists. Tracheobronchial AEC were obtained via trans-laryngeal, non-bronchoscopic brushings of children through an endotracheal tube and processed as previously described (1, 2). The study was approved by St John of God Hospital's Human Ethics Committee and written consent is obtained from each participant's legal guardian after being fully informed about the nature and purpose of the study. All experiments were performed in accordance with the relevant committees' guidelines and regulations.

Cell Culture and Reagents

Bronchial epithelial basal medium (BEBM™) and bronchial epithelial cell growth medium (BEGM™) were purchased from LONZA (Basel, Switzerland). Cell cultures were expanded as previously published (Martinovich, K. M., Iosifidis, T., et al. Sci Rep 2017; 7: 17971). Collagen type I and FN were purchased from BD (Franklin Lakes, N.J., USA) and tissue culture plastic ware were purchased from Corning (Corning, N.Y., USA).

Compounds

Celecoxib and commercially available analogues or fragments of celecoxib were purchased from Sigma-Aldrich (St. Louis, Mo., USA), SelleckChem (Houston, Tex., USA) and Toronto Research Chemicals (Toronto, ON, Canada). Compound names and chemical structures (i.e. SMILES) are listed in Table 5.

Cell Viability

Cell viability was assessed using a 3-[4,5-dimethylthiazol-2yl]-5-[3-carboxymethoxyphenyl]-2-[4-sulfophenyl]-2H-tetrazolium inner salt (MTS) assay (Promega, Madison, Wis., USA). Once confluent, cell cultures were treated with 10 μM compound, DMSO vehicle (0.05% v/v) or untreated for 48 hours.

Scratch Wound Repair Assay

To assess in vitro wound repair kinetics, linear scratch wounds were created using a commercial monolayer wounding kit. Once confluent, cell cultures were placed in starvation media (BEGM™ without epidermal growth factor) for about 24 hours prior to wounding. At the time of wounding, cell cultures were treated with compound dilution (10 μM), DMSO vehicle (0.05% v/v) or untreated. Wound closure rates were calculated through image analysis by the accompanying live-cell imaging system (Essen Bioscience, Ann Arbor, Mich., USA).

TABLE 5

Celecoxib, commercially-available analogues of celecoxib and compound fragments

| Compound Identifier | Compound Name | Chemical Structures (SMILES) |
|---|---|---|
| C22 | SC-58125 | FC(C=C1)=CC=C1C2=CC(C(F)(F)F)=NN2C3=CC=C(S(=O)(C)=O)C=C3 |
| C21 | Valdecoxib | O=S(=O)(N)C3CCC(C2C(ONC2C1CCCCC1)C)CC3 |
| C20 | Rofecoxib | CS(=O)(=O)C1=CC=C(C=C1)C1=C(C(=O)OC1)C1=CC=CC=C1 |

TABLE 5-continued

Celecoxib, commercially-available analogues of celecoxib and compound fragments

| Compound Identifier | Compound Name | Chemical Structures (SMILES) |
|---|---|---|
| C19 | 3-Trifluoromethy1-5-(p-tolyl)-1H-pyrazole | CC1=CC=C(C=C1)C2=NNC(=C2)C(F)(F)F |
| C18 | SC-58236 | ClC(C=C3)=CC=C3C1=CC(C(F)(F)F)=NN1C2=CC=C(S(=O)(N)=O)C=C2 |
| C17 | Sulfanilamide | NC1=CC=C(C=C1)S(N)(=O)=O |
| C16 | OSU-03012 (AR-12) | C1=CC=C2C(=C1)CC3=C2C=CC(=C3)C4=CC(=NN4C5=CC=C(C=C5)NC(=O)CN)C(F)(F)F |
| C15 | Sulfasalazine | C1=CC=NC(=C1)NS(=O)(=O)C2=CC=C(C=C2)N=NC3=CC(=C(C=C3)O)C(=O)O |
| C14 | Parecoxib Sodium | CCC(=O)[N-]S(=O)(=O)C1=CC=C(C=C1)C2=C(ON=C2C3=CC=CC=C3)C.[Na+] |
| C13 | Piroxicam | CN1C(=C(C2=CC=CC=C2S1(=O)=O)O)C(=O)NC3=CC=CC=N3 |
| C12 | NS-398 | CS(=O)(=O)NC1=C(C=C(C=C1)[N+](=O)[O-])OC2CCCCC2 |
| C11 | 4-[2-[1-(4-Methylphenyl) ethylidene[hydrazinyl] benzenesulfonamide | CC1=CC=C(C=C1)C(=NNC2=C(C=C(C=C2)S(=O)(=O)N[N+](=O)[O-])C |
| C10 | Hydroxy Celecoxib | CC1=CC=C(C=C1)C2=CC(=NN2C3=CC=C(C=C3)S(=O)(=O)N)C(F)(F)F |
| C9 | Deracoxib | COC1=C(F)C=C(C=C1)C1=CC(=NN1C1=CC=C(C=C1)S(N)(=O)=O)C(F)F |
| C8 | 4-Desmethyl-3-methyl Celecoxib | CC1=CC=CC(=C1)C2=CC(=NN2C3=CC=C(C=C3)S(=O)(=O)N)C(F)(F)F |
| C7 | N-De(4-sulfonamidophenyl)-N'-(4-sulfonamidophenyl) Celecoxib | CC1=CC=C(C=C1)C2=NN(C(=O2)C(F)(F)F)C3=CC=C(C=C3)S(=O)(=O)N |
| C6 | 2,5-Dimethyl-Celecoxib | CC1=CC=C(=C(C=C1)C)C2=CC(=NN2C3=CC=C(C=C3)S(=O)(=O)N)C(F)(F)F |
| C5 | Desmethyl Celecoxib (CAY10452) | C1=CC=CC(=C1)C2=CC(=N[N]2C3=CC=C(C=C3)[S](=O)(=O)N)C(F)(F)F |
| C4 | Celecoxib Carboxylic Acid | C1=CC(=CC=C1C2=CC(=NN2C3=CC=C(C=C3)S(=O)(=O)N)C(F)(F)F)C(=O)O |
| C3 | Celecoxib | CC1=CC=C(C=C1)C2=CC(=NN2C3=CC=C(C=C3)S(=O)(=O)N)C(F)(F)F |
| C2 | Benzenesulfonamide | C1=CC=C(C=C1)S(=O)(=O)N |
| C1 | SC-560 | COC1=CC=C(C=C1)N1N=C(C=C1C1=CC=C(Cl)C=C1)C(F)(F)F |

Results

Figure 11:
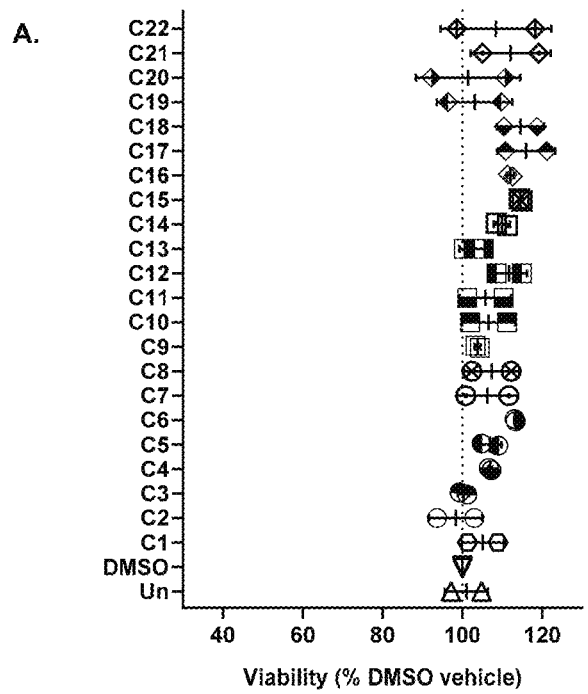
FIG. 11. Cell viability of pAEC from non-asthmatic (A) and asthmatic (B) children following 48 hours exposure to DMSO vehicle (0.05% v/v) or compound dilution (10 μM). Cell cultures from 2 non-asthmatic children, mean±SD.
Figure 11:
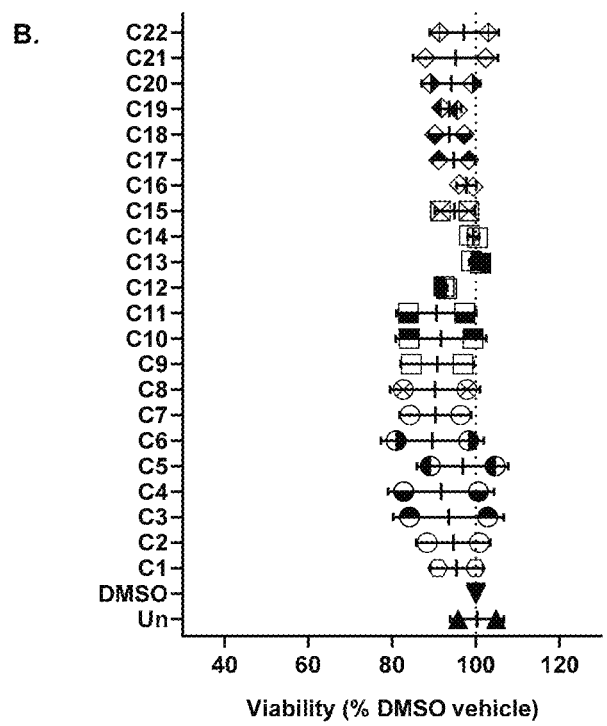
Figure 12:
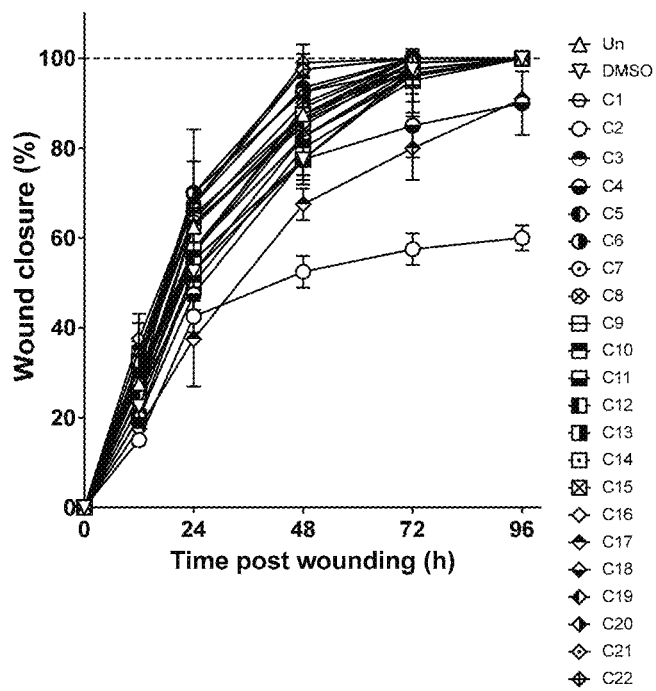
FIG. 12. Wound closure rates of pAEC from non-asthmatic children following treatment with DMSO vehicle (0.05% v/v) or compound dilution (10 μM). (A) Wound closure rates at all time points, or (B) at 48 hours only. Cell cultures from 2 non-asthmatic children, mean±SD. Dotted lines indicate the minimum and maximum wound closure rates of the DMSO vehicle control 48 hours post wounding.
Figure 12:
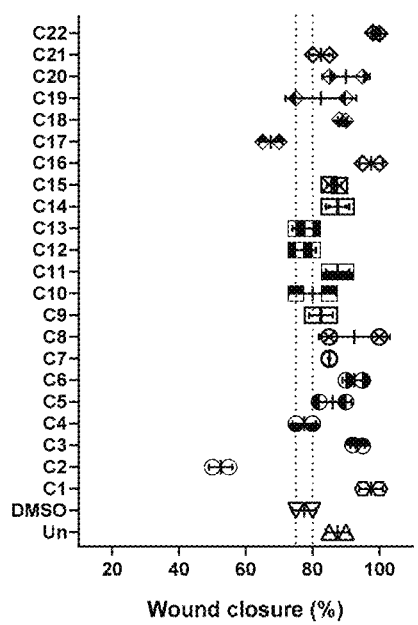

Celecoxib Analogues and Fragments are not Cytotoxic in Primary Airway Epithelial Cells Primary airway epithelial cell (pAEC) cultures from non-asthmatic (FIG. 11A) and asthmatic children (FIG. 11B) did not display any change in cell viability following celecoxib treatment for 48 hours. A change to cell viability following compound treatment relative to DMSO vehicle, of less than or equal to 20% was considered non-cytotoxic Differential Regulation of Wound Repair by Celecoxib Analogues in Non-Asthmatic pAEC Overall, the pAEC response to wounding following treatment with celecoxib compounds was varied with some compounds accelerating repair as early as 12 hours post wounding (FIG. 12A). A number of celecoxib analogues (i.e. C1, C3, C6, C16, C22) accelerated repair in pAEC from non-asthmatic children (FIG. 12A), where at least 20% increased wound closure was observed at 48 hours post wounding compared to DMSO vehicle (FIG. 12B). Other analogues (i.e. C4, C10, C12, C13) showed an improvement in wound repair of 10-20% compared to DMSO vehicle (FIG. 12B). Whilst two celecoxib fragments, C2 and C17, had a negative effect on wound repair of 10-25% compared to DMSO vehicle (FIG. 12B).

Figure 13:
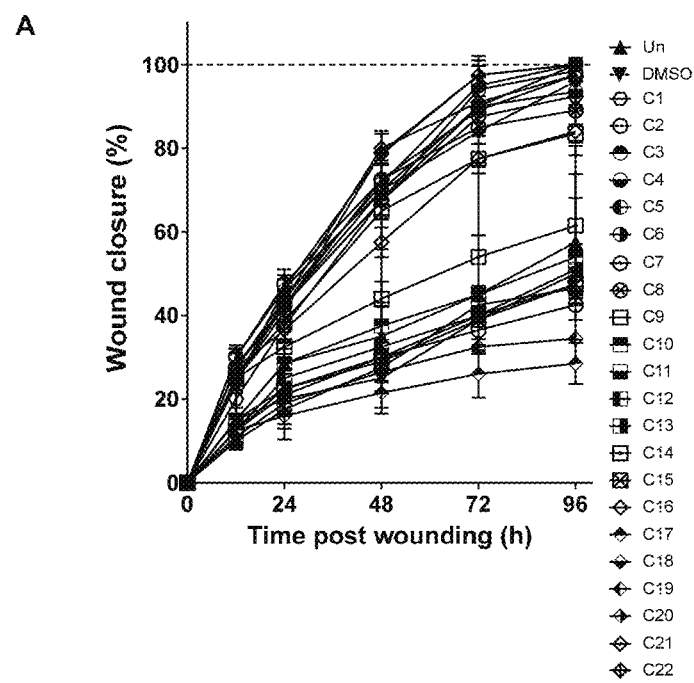
FIG. 13. Wound closure rates of pAEC from asthmatic children following treatment with DMSO vehicle (0.05% v/v) or compound dilution (10 μM). (A) Wound closure rates at all time points, or (B) at 48 hours only. Cell cultures from 2 asthmatic children, mean±SD. Dotted lines indicate the minimum and maximum wound closure rates of the DMSO vehicle control 48 hours post wounding.
Figure 13:
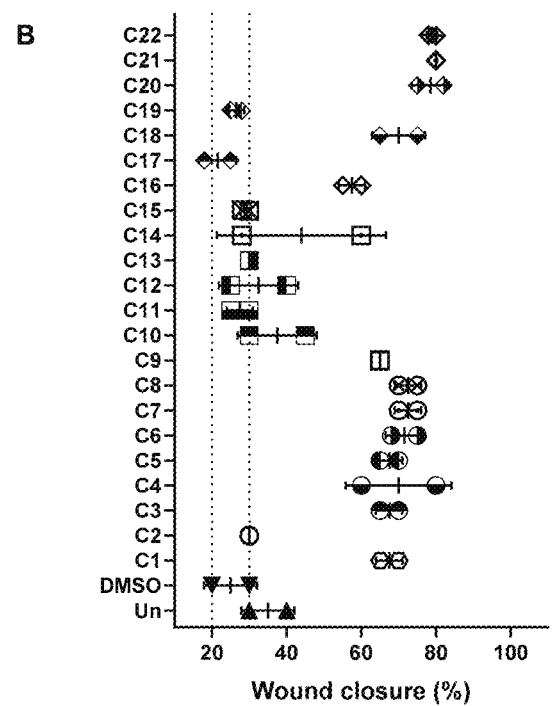
Figure 14:
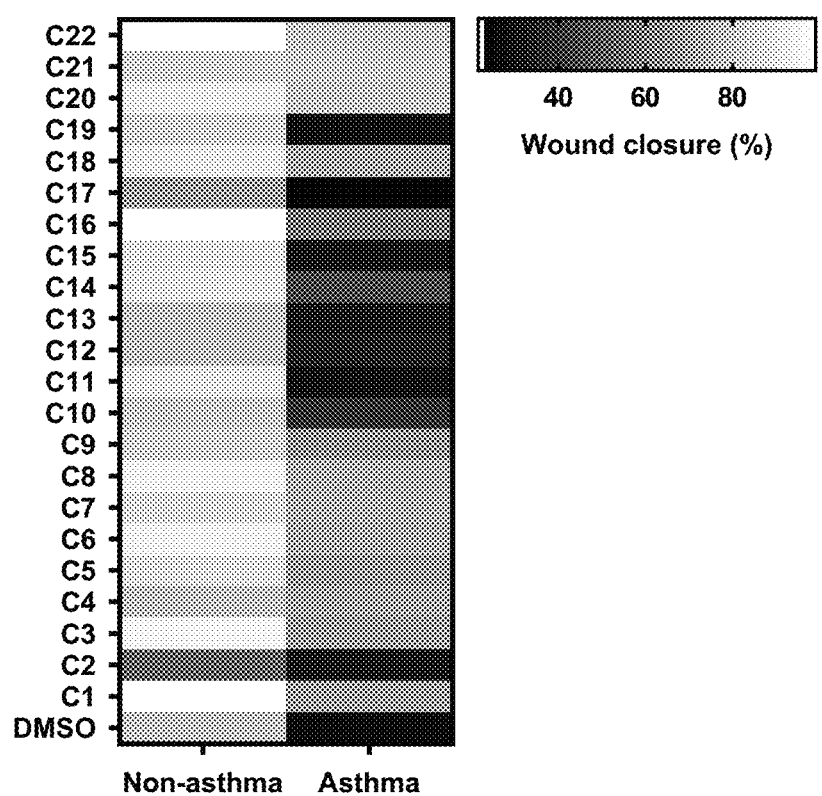
FIG. 14. Heatmap of wound closure rates of pAEC from asthmatic children at 48 hours post wounding and treatment with DMSO vehicle (0.05% v/v) or compound dilution (10 μM). Data is presented as median wound closure rates of two pAEC cultures from non-asthmatic and asthmatic children.

Differential Regulation of Wound Repair by Celecoxib Analogues in Asthmatic pAEC Cell cultures from asthmatic children have a defective repair capacity that can be modulated by celecoxib analogues by 12 hours post wounding (FIG. 13A). Most celecoxib analogues (i.e. C1, C3, C4, C5, C7, C8, C9, C16, C18, C20, C21, C22) accelerated repair in pAEC from asthmatic children at 48 hours treatment post wounding by at least 140% compared to DMSO vehicle (FIG. 13B). Three compounds (i.e. C10, C12, C14) accelerated wound repair by at least 60% in pAEC from one patient only compared to DMSO vehicle (FIG. 13B). A number of analogues (i.e. C2, C11, C13, C15, C17, C19) showed no improvement in wound repair of treated asthmatic pAEC compared to DMSO vehicle (FIG. 13B). Despite different repair responses between compound treated pAEC cultures of non-asthmatic and asthmatic children, common compounds were found to be least (e.g. C2, C17) or maximally effective (FIG. 14).

Through screening of celecoxib, celecoxib analogues and fragments the inventors identified compounds that accelerate pAEC repair in vitro. Furthermore, these data highlight compounds that promote epithelial a repair to a greater degree than celecoxib, such as SC-58125. The modulatory effects of celecoxib on pAEC repair are not COX-2-inhibition dependent, for example because desmethyl celecoxib, celecoxib and 2,5-dimethyl celecoxib show comparable efficacy to enhance pAEC repair.

Example 6: Discussion

This study provides new insights regarding mechanisms regulating airway epithelial repair, in the context of childhood asthma. Analysis of the cell migration of leading edge cells during in vitro repair supported the hypothesis that defective cell migration patterns impair the capacity of asthmatic airway epithelial cells to repair a wound. Global transcriptomic profiling was performed using RNA-Seq in wounded pAEC samples from children and identified transcriptional alterations in the integrin signaling pathway. Thorough profiling of FN-binding integrin expression of ex vivo and in vitro pAEC of children, as well as investigation of the role of integrin $\alpha5\beta1$ during in vitro wound repair determined that dysregulated expression of integrin $\alpha5\beta1$ in the asthmatic epithelium impairs airway epithelial cell migration and subsequent repair. Furthermore, activation of the PI3K/Akt pathway in pAEC from children with asthma was found to upregulate integrin $\alpha5\beta1$ and enhance epithelial cell migration and repair following wounding. The data provide mechanism-based evidence that Celecoxib and its analogue, dimethyl-Celecoxib, are potential candidates to enhance epithelial repair in the airways of children with asthma. Collectively, these unique observations support the theory that intrinsic differences in the asthmatic airway epithelium drive the dysregulated airway epithelial repair observed. Importantly, this study has contributed to our understanding of epithelial biology and asthma, as well as identified potential novel therapeutic targets to aid epithelial repair in patients with asthma.

This the first study to report the migration patterns of primary airway epithelial cells in response to injury. Using a submerged monolayer airway epithelial culture model coupled with frequent time-lapse imaging and manual tracking of leading edge cells over the first 12 h post wounding, this study was able to interrogate the initiating phase of the wound response, re-epithelialization via collective sheet migration. Significantly, pAEC of children with asthma displayed defective migration following in vitro wounding, that is decreased distance, velocity, directionality and forward migration suggesting that a loss of initiation and coordination of re-epithelialization could compromise epithelial barrier restitution and initiate a vicious cycle of damage, insufficient repair and inflammation. The findings of this study could relate to other chronic airway diseases, such as CF, COPD, and IPF, that have been shown to have a dysregulated response to injury. It is likely that abnormalities in the cell-matrix interactions and defective leading edge cell migration exist in the airway epithelia of chronically inflamed and vulnerable airways. In fact, altered integrin expression has been reported in the airways of patients with severe asthma and IPF. Thus, therapeutic targeting airway epithelial repair via modulation of integrin expression is expected suitable in a variety of chronic airway diseases, including but not limited to cystic fibrosis, chronic obstructive pulmonary disease (COPD), idiopathic pulmonary disease, bronchiolitis, bronchiolitis obliterans, bronchopulmonary disorder (BPD).

The data presented herein provide evidence that the expression of integrin $\alpha5\beta1$ dictates the migration and repair response in airway epithelial cells of children. In fact, it has been previously demonstrated that inhibition of FN or FN-binding integrin $\alpha5\beta1$ was sufficient to abrogate nasal epithelial repair in vitro. It has been previously shown that the asthmatic airway epithelium expresses lower levels of FN at baseline and post wounding compared to their non-asthmatic counterparts. Furthermore, although exogenous FN supplementation aided asthmatic airway epithelial repair, it did not result in complete wound closure. This study utilized RNA-Seq of leading edge samples to elucidate the central abnormalities present in migrating cells from children with asthma compared to non-asthmatic children. Indeed, the importance of integrins and further upstream, the role of PI3K-Akt signaling to regulate cell migration and repair were identified. Importantly, this study found that Akt signaling is dampened in pAEC of children with asthma, which inhibits the downstream expression of integrin $\alpha5\beta1$ and effective cell migration and repair. To date, PI3K-Akt signaling has been demonstrated to be a key regulator of cell migration and repair, where enhanced PI3K-Akt accelerates wound healing and cancer metastasis and loss of PI3K-Akt inhibits cell migration and repair. Thus, although uncontrolled Akt signaling can lead to a variety of cancers, induction of this pathway in response to damage is fundamental for coordinating wound re-epithelialization and barrier restitution. For the first time, complete wound closure of the asthmatic airway epithelium was achieved in this study via the activation of the PI3K-Akt-integrin $\alpha5\beta1$ pathway axis. Current treatments for asthma focus on targeting the excessive bronchoconstriction symptoms and eosinophilic inflammation with the use of bronchodilators and corticosteroids, which may have negative impact on epithelial repair. Novel therapeutic strategies are necessary that target the underlying abnormalities in asthma, such as defective epithelial repair, to prevent further damage, inflammation and remodeling.

The data presented herein provide evidence that the FDA-approved nonsteroidal anti-inflammatory drug celecoxib (Celebrex) and its analogue, dimethyl-Celecoxib that lacks inhibitory activity to COX2 enzymes, which are currently not considered for treatment any chronic lung inflammatory diseases, stimulate the PI3K/Akt/integrin $\alpha5\beta1$ pathway axis, enhancing airway epithelial cell migration and repair in cultures of children with asthma. The fact that the dimethyl-Celecoxib analogue has favorable effects in cultures of children with asthma suggests that celecoxib's mechanism/s of action may be independent of inhibition of COX2 enzymes. Nevertheless, the anti-inflammatory effects of celecoxib is beneficial in asthma and other chronic lung diseases that are prone to high levels of inflammation, and could potentially reduce required dosage of corticosteroid treatment if taken as a combination therapy although that needs to be determined. Celebrex is already approved for use in children with juvenile arthritis that could translate to a quicker repurposing for treatment of children with asthma. It should be noted that, although Celebrex has a warning of increased risk of myocardial infarction, these adverse cardiovascular events appear less frequently in users of celecoxib than other classical NSAIDs like Ibuprofen as recently demonstrated by a large randomized clinical trial at the Cleveland Clinic. Furthermore, these adverse events occurred in adults taking high doses for extended periods of time. Therefore, reduced doses and modified route of administration such as aerosolized therapy could mitigate these concerns. Importantly, aerosolized formulations of NSAIDs, such as Ibuprofen and Celebrex, have already been proven to be effective in controlling inflammation and lung cancer tumor growth respectively.

This study utilized two well-characterized methods of airway epithelial cell cultures, that is BEGM and conditional reprogramming methods to investigate the mechanisms underlying the dysregulated response to wounding in primary cell cultures from healthy children and children with asthma. Significantly, the fact that defective cell migration and repair following in vitro wounding are conserved in different models of airway epithelial cell cultures highlights the strength of these culture methods and the biological significance of intrinsic differences in the airway epithelium of children with asthma. Advantageously, airway cells obtained from an individual with asthma may be used in the future to test the efficacy of repurposed and new compounds to improve airway epithelial restitution and personalize treatment.

In summary, this study has identified an intrinsic abnormality in the capacity of the airway epithelium to migrate during wound reepithelization due to inhibited signaling via the PI3K-Akt pathway and reduced expression levels of integrin $\alpha5\beta1$. This study identified a mechanism that is able to restore repair of the airway epithelium of asthmatics. Currently available and FDA-approved compounds, such as Celebrex, that activate Akt signaling and restore integrin $\alpha5\beta1$ expression can be repurposed to accelerate wound healing in the airways of asthmatics, minimizing chronic inflammation and preventing further damage to the airways. Thus, the finding that PI3K/Akt increases integrin $\alpha5\beta1$ and repair is clinically relevant, and agents that regulate epithelial repair via the PI3K-Akt-$\alpha5\beta1$ axis are potential novel drugs for preventing airway damage, aid epithelia repair and improve long-term health outcomes by targeting the underlying pathogenic mechanisms of asthma. Collectively, this investigation has provided new insight regarding important intrinsic epithelial vulnerability in asthma, identified Celecoxib as a novel therapy for asthma and has provided further rational for investigating epithelium-centered asthma therapies in young children with asthma.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for promoting epithelium repair in a subject, the method comprising administering to the subject a therapeutically effective amount of an activator of PI3K/Akt signalling, wherein the activator is selected from celecoxib, dimethyl-celecoxib, SC-58125 (5-(4-fluorophenyl)-1[4-(methylsulfonyl)phenyl]-3-(trifluoromethyl)-1H-pyrazole), valdecoxib, rofecoxib, 3-trifluoromethyl-5-(p-tolyl)-1H-pyrazole, SC-58236 (4-[5-(4-chlorophenyl)-3-(trifluoromethyl)-1H-pyrazol-1-yl]benzenesulfonamide), OSU-03012 (AR-12,2-Amino-N-[4-[5-(2-phenanthrenyl)-3-(trifluoromethyl)-1H-pyrazol-1-yl]phenyl]acetamide), sulfasalazine, parecoxib sodium, piroxicam, NS-398 (N-[2-(Cyclohexyloxy)-4-nitrophenyl]methanesulfonamide), 4-[2-[1-(4-methylphenyl) ethylidene]hydrazinyl] benzenesulfonamide, hydroxy celecoxib, deracoxib, 4-desmethyl-3-methyl celecoxib, N-de(4-sulfonamidophenyl)-N'-(4-sulfonamidophenyl) celecoxib, 2,5-dimethyl-celecoxib, desmethyl celecoxib, celecoxib carboxylic acid, and SC-560 (5-(4-Chlorophenyl)-1-(4-methoxyphenyl)-3-trifluoromethyl pyrazole).

2. The method of claim 1, wherein the epithelium is airway epithelium.

3. The method of claim 2, wherein the epithelium is stratified epithelium of the skin.

4. The method of claim 1, wherein the activator enhances expression of a5⊖1 integrin in an epithelial cell of the subject.

5. The method of claim 1, wherein the subject is a smoker.

6. The method of claim 1, wherein the promotion of epithelial repair in the subject slows or reduces the progression of a disease or condition in the subject, and wherein the disease or condition is selected from one or more of asthma, diabetes, peripheral vascular disease, an autoimmune disorder, chronic inflammation, acute inflammation, a wound, or stress.

7. The method of claim 1, wherein the subject is an infant or child.

8. The method of claim 1, wherein the subject is an asthmatic child.

* * * * *